US010322097B2

(12) United States Patent
Wong et al.

(10) Patent No.: US 10,322,097 B2
(45) Date of Patent: Jun. 18, 2019

(54) TREATMENT OF SUBJECTS WITH MULTIDRUG-RESISTANT CANCER

(71) Applicant: Macau University of Science and Technology, Taipa Macau (CN)

(72) Inventors: Kam Wai Wong, Taipa (CN); Yuen Kwan Law, Taipa (CN); Thomas Efferth, Mainz (DE); Su-Wei Xu, Taipa (CN); Sami Hamdoun, Taipa (CN); Liang Liu, Taipa (CN)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 0 days.

(21) Appl. No.: 14/971,153

(22) Filed: Dec. 16, 2015

(65) Prior Publication Data

US 2017/0128394 A1 May 11, 2017

Related U.S. Application Data

(60) Provisional application No. 62/251,189, filed on Nov. 5, 2015.

(51) Int. Cl.
| | | |
|---|---|---|
| *A61K 31/19* | (2006.01) | |
| *A61K 31/337* | (2006.01) | |
| *A61K 31/553* | (2006.01) | |
| *A61K 31/704* | (2006.01) | |
| *A61K 31/7048* | (2006.01) | |
| *A61K 33/24* | (2019.01) | |

(52) U.S. Cl.
CPC ............ *A61K 31/19* (2013.01); *A61K 31/337* (2013.01); *A61K 31/553* (2013.01); *A61K 31/704* (2013.01); *A61K 31/7048* (2013.01); *A61K 33/24* (2013.01)

(58) Field of Classification Search
CPC .... A61K 31/19; A61K 31/337; A61K 31/553; A61K 31/704
See application file for complete search history.

(56) References Cited

U.S. PATENT DOCUMENTS

2011/0263693 A1* 10/2011 Vinson-Hieronymus .................. A61K 31/203
514/453

OTHER PUBLICATIONS

Sethi et al. (Blood. 2007;109: 2727-2735).*
Raja et al. Cancer Biology & therapy (2011) 11(2); 263-276.*
Jie et al. (The practical J. of Cancer (Mar. 2011) Abstract Only.*
Kennedy et al. (Chemistry & Biodiversity; 8, 2291-2298; (2011).*
McCurrach et al. (Proc. Natl. Acad. Sci. 94; 2345-2349 (1997).*
Lu et al. (Mol. Cancer; 2010: 9: 112).*
Han, L., et al. Non-alkaloids extract from Stemona sessilifolia enhances the activity of chemotherapeutic agents through P-glycoprotein-mediated multidrug-resistant cancer cells. Nat Prod Res, 1-4 (2015).
Callaghan, R., Luk, F. & Bebawy, M. Inhibition of the multidrug resistance P-glycoprotein: time for a change of strategy? Drug Metab Dispos 42, 623-631 (2014).
Aller, S.G., et al. Structure of P-glycoprotein reveals a molecular basis for poly-specific drug binding. Science 323, 1718-1722 (2009).
Kim, T.H., et al. Resveratrol enhances chemosensitivity of doxorubicin in multidrug-resistant human breast cancer cells via increased cellular influx of doxorubicin. Biochim Biophys Acta 1840, 615-625 (2014).
Xu, L. et al. Enhanced activity of doxorubicin in drug resistant A549 tumor cells by encapsulation of P-glycoprotein inhibitor in PLGA-based nanovectors. Oncol Lett 7, 387-392 (2014).
Xing, Y., Wang, Z.H., Ma, D.H. & Han, Y. FTY720 enhances chemosensitivity of colon cancer cells to doxorubicin and etoposide via the modulation of P-glycoprotein and multidrug resistance protein 1. J Dig Dis 15, 246-259 (2014).
Westphal, D., Dewson, G., Czabotar, P.E. & Kluck, R.M. Molecular biology of Bax and Bak activation and action. Biochimica et Biophysica Acta (BBA)—Molecular Cell Research 1813, 521-531 (2011).
Brown, J.M. & Wouters, B.G. Apoptosis, p53, and tumor cell sensitivity to anticancer agents. Cancer research 59, 1391-1399 (1999).
Gudkov, A.V. & Komarova, E.A. The role of p53 in determining sensitivity to radiotherapy. Nature Reviews Cancer 3, 117-129 (2003).
Branch, P., Masson, M., Aquilina, G., Bignami, M. & Karran, P. Spontaneous development of drug resistance: mismatch repair and p53 defects in resistance to cisplatin in human tumor cells. Oncogene 19, 3138-3145 (2000).
Fan, S. et al. p53 gene mutations are associated with decreased sensitivity of human lymphoma cells to DNA damaging agents. Cancer research 54, 5824-5830 (1994).
Tajima, Y., et al. Nitensidine A, a guanidine alkaloid from Pterogyne nitens, is a novel substrate for human ABC transporter ABCB1. Phytomedicine : international journal of phytotherapy and phytopharmacology 21, 323-332 (2014).
Morris, G.M., et al. AutoDock4 and AutoDockTools4: Automated Docking with Selective Receptor Flexibility. J Comput Chem 30, 2785-2791 (2009).

(Continued)

*Primary Examiner* — Shirley V Gembeh
(74) *Attorney, Agent, or Firm* — Renner Kenner Greive Bobak Taylor & Weber

(57) ABSTRACT

A quinonemethide triterpenoid is administered to subjects with multidrug-resistant cancer, in particular a cancer with enhanced expression and/or functional activity of ABC transporter proteins such as P-glycoprotein and/or an apoptosis-deficient, in particular p53-, Bax- or Bak-deficient, cancer, i.e. specific subgroups of subjects with cancer. The quinonemethide triterpenoid is suitable to treat cancer allowing for an accumulation of cytotoxic or therapeutic compounds in the cells while having exceptionally increased cytotoxic activity towards the multidrug-resistant cancer cells and while allowing for an increased activity of chemotherapeutic compounds. Methods for specifically targeting cancer cells with multidrug-resistance and methods for potentiating the activity of a chemotherapeutic compound in those cancer cells are also disclosed. A kit including a quinonemethide triterpenoid and a chemotherapeutic compound is also provided.

13 Claims, 9 Drawing Sheets

(56) References Cited

OTHER PUBLICATIONS

Efferth, T. et al. Prediction of Broad Spectrum Resistance of Tumors towards Anticancer Drugs. Clinical Cancer Research 14, 2405-2412 (2008).
Takeuchi, K. et al. RET, ROS1 and ALK fusions in lung cancer. Nature medicine18, 378-381 (2012).
Davare, M.A. et al. Foretinib is a potent inhibitor of oncogenic ROS1 fusion proteins. Proceedings of the National Academy of Sciences of the United States of America110, 19519-19524 (2013).
Sang, J. et al. Targeted inhibition of the molecular chaperone Hsp90 overcomes ALK inhibitor resistance in non-small cell lung cancer. Cancer discovery3, 430-443 (2013).
Friboulet, L. et al. The ALK inhibitor ceritinib overcomes crizotinib resistance in non-small cell lung cancer. Cancer discovery4, 662-673 (2014).
Gandhi, L. & Janne, P.A. Crizotinib for ALK-rearranged non-small cell lung cancer: a new targeted therapy for a new target. Clinical cancer research : an official journal of the American Association for Cancer Research18, 3737-3742 (2012).
Zou, H.Y. et al. PF-06463922 is a potent and selective next-generation ROS1/ALK inhibitor capable of blocking crizotinib-resistant ROS1 mutations. Proceedings of the National Academy of Sciences of the United States of America112, 3493-3498 (2015).
Med, S.T. Escaping ALK inhibition_ mechanisms of and strategies to overcome resistance. Lovly CM, Pao W4 (2012).
Katayama, R. et al. Therapeutic strategies to overcome crizotinib resistance in non-small cell lung cancers harboring the fusion oncogene EML4-ALK. Proceedings of the National Academy of Sciences of the United States of America108, 7535-7540 (2011).

\* cited by examiner

TREATMENT OF SUBJECTS WITH MULTIDRUG-RESISTANT CANCER

CROSS-REFERENCE TO RELATED APPLICATIONS

This application claims the benefit of U.S. Provisional Patent Application No. 62/251,189, filed Nov. 5, 2015, incorporated herein by reference.

TECHNICAL FIELD

The present invention relates in a first aspect to a method for treating a subject suffering from a multidrug-resistant cancer, i.e. a cancer with multidrug-resistant phenotype and, thus, a specific subgroup of subjects with cancer. The method comprises administrating a quinonemethide triterpenoid to said subject. In another aspect of the present invention, a method for specifically targeting tumor cells with multidrug-resistance is provided comprising contacting said cancer cells with the quinonemethide triterpenoid as well as a method of potentiating the activity of a chemotherapeutic compound in multidrug-resistant cancer cells. In a further aspect, the present invention provides a kit comprising the quinonemethide triterpenoid and a chemotherapeutic compound.

BACKGROUND OF THE INVENTION

Drug-resistance in cancer is the major impediment to a successful treatment of cancer. Multidrug-resistance (MDR) in cancer cells is a phenotype whereby cells display a reduced sensitivity to chemotherapeutic compounds based on several mechanisms in particular including an increase in drug efflux (Han, L. et al., Nat Prod Res, 2015, 1-4). Said multidrug-resistance can be a pre-existing one and, thus, evident at the onset of therapy (intrinsic) or alternatively be acquired after onset of therapy.

Members of the family of membrane proteins named ATP binding cassette (ABC transporter proteins) transporters or pumps usually consist of four domains which include two trans-membrane domains (TMDs) and two nucleotide binding domains (NBDs) as minimum functional unit to transport a substrate such as a chemotherapeutic compound triggered by ATP binding and respective hydrolysis. Members of said family are notorious mediators of MDR, actively effluxing a wide range of therapeutic compounds such as chemotherapeutic compounds irrespective of their concentration gradient. This significantly lowers their intracellular concentration and, thus, their therapeutic effect in those cells. A prominent ABC transporter protein subfamily reported to modulate anticancer drug uptake is the "B" subfamily in particular with P-glycoprotein (P-gp, MDR1, or ABCB1) or ABCB5 including respective isoforms. Besides, common ABC transporters include the "C" subfamily such as with multidrug-resistance protein (MRP1 or ABCC1) and the "G"-subfamily such as with breast cancer resistance protein (ABCG2 or MXR).

ABC transporter proteins have been found to be constitutively expressed and overexpressed, respectively, in many multidrug-resistant cancers, wherein P-glycoprotein is considered for being a key player in the multidrug-resistant phenotype in cancer. Thereby, the expression of P-glycoprotein in multidrug-resistant cancer cells seems to be regulated by a wide range of factors including hypoxia, metabolic acidosis, generation of reactive oxygen species, namely P-glycoprotein is considered for being an important responder to chemical insult or environmental influences on cancer (Callaghan, R. et al., Drug Metab Dispos 2014, 42:623-31).

Expression and overexpression, respectively, of P-glycoprotein has been found in various types of cancers and cancer cells, respectively, with the multidrug-resistant phenotype, such as MCF-7 breast (Kim, T. H. et al., Biochim Biophys Acta, 2014, 1840:615-25, A549 lung cancer (Xu, L. et al., Oncol Lett, 2014, 7:387-392), and HCT-8 colon cancer (Xing, Y. et al., J Dig Dis, 2014, 15:246-59). Such expression and overexpression, respectively, of P-glycoprotein is usually accompanied by a resistance against commonly used and standard chemotherapeutic compounds such as anthracyclines, vinca alkaloids, topoisomerase-I and -II inhibitors, taxanes and the like, for example against doxorubicin or paclitaxel (taxol). Its broad specificity has been the subject of major attempts to inhibit said protein pump activity and to sensitize the cells towards chemotherapeutic compounds (Callaghan, R. et al., Drug Metab Dispos 2014, 42:623-31). Accordingly, a strategy is to identify small-molecules that either act as direct P-glycoprotein inhibitors or compete with chemotherapeutic compounds for transport. Furthermore, the resolved structure of P-glycoprotein further revealed a molecular basis for poly-specific drug binding crucial for the lead optimization of chemotherapeutic compounds and MDR modulators (Aller, S. G. et al., Science, 2009, 323: 1718-22).

MDR modulators developed so far, however, fail to provide sufficient inhibition of ABC transporter proteins such as P-glycoprotein and/or did not demonstrate sufficient clinical utility in overcoming multidrug-resistance. Besides, most of the ABC transporter protein inhibitors described so far have been initially developed for the treatment of other diseases than cancer like verapamil and these main drug activities may, thus, appear as non-tolerable side effects in cancer therapy. Unfortunately, progress in this area has been rather slow although having effective treatment options for multidrug-resistant cancer gets more and more important today.

Pro- and anti-apoptotic proteins have been associated with multi-drug resistant cancer, too. Apoptosis is a defined program of cell death with molecular and morphologic changes such as DNA fragmentation, formation of cytoplasmic apoptotic bodies and plasma membrane changes. It is markedly influenced by various genes and respective proteins, which may be mutated or dysfunctionally regulated such as pro-apoptotic proteins may be absent or there may be an enhanced expression of anti-apoptotic proteins or mutations which inactivate pro-apoptotic proteins and activate anti-apoptotic proteins in cancer cells. In this context, it has been especially found that the expression of mutant and wild-type p53 or Bcl-2-family members and other proteins associated with the control of apoptosis in cells may have a significant impact on the clinical sensitivity of cancer cells. Thus, these proteins are also possible targets in order to overcome multidrug-resistance. For example, cancer cells lacking cell death mediators Bax and Bak have been reported to develop drug-resistance to elude various apoptosis-stimuli (Westphal, D. et al., Biochimica et Biophysica Acta (BBA)-Molecular Cell Research, 2011, 1813:521-531). Apart from the apoptotic proteins, pro-apoptotic tumor suppressor protein p53 proved to be a sensor of cellular stress and also a critical initiator of apoptosis (Gudkov, A. V. and Komarova, E. A., Nature Reviews Cancer 2003, 3:117-129). The high frequency of p53 mutations is expected to lead to a drug resistance of cancer cells, too (Branch, P. et al., Oncogene, 2000, 19:3138-3145, Fan, S. et al. Cancer research, 1994, 54:5824-5830).

Consequently, there is a strong need for methods and means allowing for an effective therapeutic treatment especially of multidrug-resistant cancer and cancer cells with a multidrug-resistant phenotype, respectively. In particular, efficacious treatment options are urgently required for specifically treating subjects with multidrug-resistant cancer with expression or overexpression of ABC transporter proteins, decreased expression of pro-apoptotic proteins and/or increased expression of anti-apoptotic proteins, i.e. for treating said specific subgroups of subjects among subjects with cancer.

SUMMARY OF THE INVENTION

The present invention relates in a first aspect to a method for treating a subject suffering from multidrug-resistant cancer, i.e. a cancer with multidrug-resistant phenotype, especially ABC-protein-dependent, in particular P-glycoprotein-dependent cancer or cancer being apoptosis-deficient, in particular being at least one of p53-deficient, Bax-deficient or Bak-deficient. Said method of treating the subject with multidrug-resistant cancer comprises the step of administering an effective amount of a quinonemethide triterpenoid to said subject.

The quinonemethide triterpenoid administered according to the present invention has a structure of Formula (I) including any salt, solvate or anhydrate thereof:

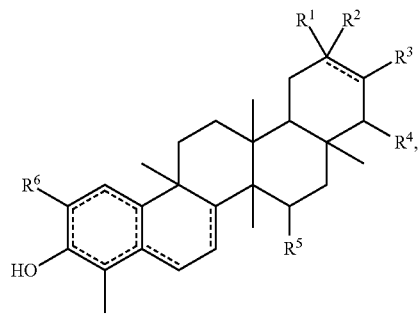

Formula (I)

wherein

⸺ represents a single or double bond.

$R^1$ is selected from —$CH_3$, —$CH_2OH$, —OH or —H;

$R^2$ is selected from —$CH_3$, —$CH_2OH$, —OH, —COOH, —$COOCH_3$, =$CH_2$ or —H;

$R^3$ is selected from —OH, =O or —H;

$R^4$ is selected from —OH or —H;

$R^5$ is selected from —OH or —H;

$R^6$ is selected from =O or OH.

In particular, the quinonemethide triterpenoid of the present invention has a structure of Formula (II):

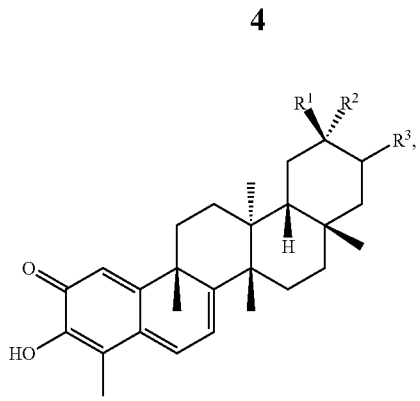

Formula (II)

wherein $R^1$ is selected from —$CH_3$, or —$CH_2OH$;

$R^2$ is selected from —COOH or —$COOCH_3$;

$R^3$ is selected from —OH, =O or —H.

More preferably, the quinonemethide triterpenoid of the present invention has a structure of Formula (IIIa):

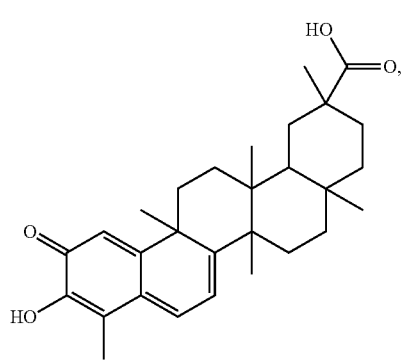

Formula (IIIa)

in particular a structure of Formula (IIIb):

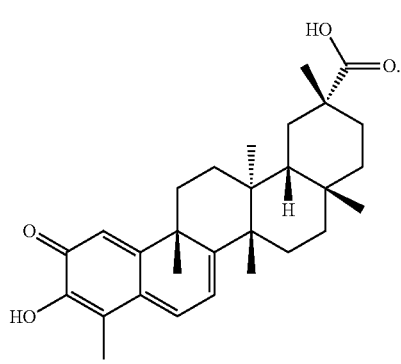

Formula (IIIb)

The quinonemethide triterpenoid of the present invention is in particular administered in combination with at least one further therapeutic compound used for treating cancer such as a chemotherapeutic compound, namely selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog.

According to the invention is also the quinonemethide triterpenoid described above for use as a medicament for the treatment of multidrug-resistant cancer, in particular ABC-protein-dependent such as P-glycoprotein-dependent multidrug-resistant cancer or apoptosis-deficient such as p53-deficient, Bax-deficient and/or Bak-deficient multidrug-resistant cancer. Another aspect of the invention refers to the use of the quinonemethide triterpenoid described above for preparing a medicament for treatment of multidrug-resistant cancer, in particular ABC-protein-dependent such as P-glycoprotein-dependent or apoptosis-deficient such as p53-deficient, Bax-deficient and/or Bak-deficient multidrug-resistant cancer. The quinonemethide triterpenoid described above is in particular used in combination with further therapeutic compounds, preferably therapeutic compounds which are used for treating cancer such as chemotherapeutic compounds. The present invention also relates to the use of the quinonemethide triterpenoid as described above as P-glycoprotein inhibitor for treating multidrug-resistant cancer.

In another aspect of the present invention, a method for specifically targeting cancer cells with multidrug-resistance is provided, in particular ABC-protein-dependent such as P-glycoprotein-dependent or apoptosis-deficient such as p53-deficient, Bax-deficient and/or Bak-deficient multidrug-resistant cancer cells. Said method comprises the step of contacting a population of multidrug-resistant cancer cells with a quinonemethide triterpenoid as described above or a salt, solvate or anhydrate thereof. In particular, the growth of the tumor cells is suppressed and/or cell death is induced.

Said method for specifically targeting cancer cells with multidrug-resistance may further comprise contacting said cells with a further therapeutic compound, in particular a compound used for treating cancer such as a chemotherapeutic compound before, simultaneously with or subsequent to the application of the quinonemethide triterpenoid as described above.

In still another aspect, the present invention provides a method of potentiating the activity of a chemotherapeutic compound in multidrug-resistant cancer cells. Said method comprises contacting said cancer cells with the quinonemethide triterpenoid as described above, and with a chemotherapeutic compound commonly used for treating cancer, namely selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog, wherein said multidrug-resistant cancer cells are resistant against the chemotherapeutic compound.

Further in accordance with the present invention is a kit comprising an effective dose of the quinonemethide triterpenoid as described above and an effective dose of at least a further chemotherapeutic compound commonly used for treating cancer, namely selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog. The kit may further comprise excipients, in particular pharmaceutically acceptable excipients, such as a carrier, salt, buffer, water, or a combination thereof.

Accordingly, the present invention provides a novel and highly advantageous way for treating multidrug-resistant cancers from various origins including either (i) the administration of the quinonemethide triterpenoid as described above or (ii) of the quinonemethide triterpenoid as described above as an adjuvant agent in combination with other chemotherapeutic compounds, in particular those being substrates of at least one ABC-protein, in particular of P-glycoprotein. It has been found that the quinonemethide triterpenoid of the present invention in particular of Formula (II), (IIIa) or (IIIb) is especially suitable for inhibiting ABC protein activity, in particular P-glycoprotein activity leading to an accumulation of cytotoxic compounds or therapeutic compounds in said cancer cells while having exceptionally increased cytotoxic activity specifically towards multidrug-resistant cancer cells such as various human cancer cells. Said quinonemethide triterpenoid described above in particular allows for effectively targeting said multidrug-resistant cancer and cancer cells, respectively, either alone or in combination with conventional chemotherapeutic compounds as well as for potentiating the activity of commonly used chemotherapeutic compounds, and, thus, provides an advantageous treatment exceptionally suitable to specifically address multidrug-resistant cancer.

In particular, the quinonemethide triterpenoid of Formula (IIIb) proved to specifically and advantageously target ABC-protein such as P-glycoprotein-dependent multidrug-resistant and/or apoptosis-deficient multidrug-resistant cancer cells such as p53-deficient and Bax/Bak-deficient multidrug-resistant cancer cells through collateral sensitivity, i.e. it is especially suitable to selectively kill these multidrug-resistant cancer cells. Namely, a significantly lower dose is required for treating the multidrug-resistant cancer cells compared to cancer cells of the same cell type without a multidrug-resistant phenotype, usually the $IC_{50}$ of the quinonemethide triterpenoid towards multidrug-resistant cancer cells is significantly reduced.

BRIEF DESCRIPTION OF THE DRAWINGS

FIG. 2A shows the curve obtained with flow cytometry analysis of a Rho123 efflux assay in unstained A549 taxol-resistant lung cancer cells. FIG. 2B shows the curve obtained with flow cytometry analysis of a Rho123 efflux assay in A549 taxol-resistant lung cancer cells in the control group. FIG. 2C shows the curve obtained with flow cytometry analysis of a Rho123 efflux assay in A549 taxol-resistant lung cancer cells treated with 10 μM verapamil. FIG. 2D shows the curve obtained with flow cytometry analysis of a Rho123 efflux assay in A549 taxol-resistant lung cancer cells treated with 0.1 μM of celastrol. FIG. 2E shows the curve obtained with flow cytometry analysis of a Rho123 efflux assay in A549 taxol-resistant lung cancer cells treated with 0.2 μM of celastrol. FIG. 2F shows the curve obtained with flow cytometry analysis of a Rho123 efflux assay in A549 taxol-resistant lung cancer cells treated with 0.5 μM of celastrol. FIG. 2G shows the curve obtained with flow cytometry analysis of a Rho123 efflux assay in A549 taxol-resistant lung cancer cells treated with 1 μM of celastrol.

FIG. 4A shows the pattern obtained with Annexin V flow cytometry analysis of cell death in A549 taxol-resistant lung cancer cells of the control group. FIG. 4B shows the pattern obtained with Annexin V flow cytometry analysis of cell death in A549 taxol-resistant lung cancer cells treated with 0.1 µM celastrol. FIG. 4C shows the pattern obtained with Annexin V flow cytometry analysis of cell death in A549 taxol-resistant lung cancer cells treated with 0.2 µM celastrol. FIG. 4D shows the pattern obtained with Annexin V flow cytometry analysis of cell death in A549 taxol-resistant lung cancer cells treated with 0.5 µM celastrol. FIG. 4E shows the pattern obtained with Annexin V flow cytometry analysis of cell death in A549 taxol-resistant lung cancer cells treated with 40 µM taxol. FIG. 4F shows the pattern obtained with Annexin V flow cytometry analysis of cell death in A549 taxol-resistant lung cancer cells treated with 0.1 µM celastrol and 40 µM taxol. FIG. 4G shows the pattern obtained with Annexin V flow cytometry analysis of cell death in A549 taxol-resistant lung cancer cells treated with 0.2 µM celastrol and 40 µM taxol. FIG. 4H shows the pattern obtained with Annexin V flow cytometry analysis of cell death in A549 taxol-resistant lung cancer cells treated with 0.5 µM celastrol and 40 µM taxol.

FIG. 6A shows the curve obtained with flow cytometry analysis of a Rho123 efflux assay in A549 taxol-resistant lung cancer cells in the control group. FIG. 6B shows the curve obtained with flow cytometry analysis of a Rho123 efflux assay in A549 taxol-resistant lung cancer cells treated with 10 µM verapamil. FIG. 6C shows the curve obtained with flow cytometry analysis of a Rho123 efflux assay in A549 taxol-resistant lung cancer cells treated with 0.5 µM of celastrol. FIG. 6D shows the curve obtained with flow cytometry analysis of a Rho123 efflux assay in A549 taxol-resistant lung cancer cells treated with 0.5 µM of pristimerin. FIG. 6E shows the curve obtained with flow cytometry analysis of a Rho123 efflux assay in A549 taxol-resistant lung cancer cells treated with 0.5 µM of dihydrocelastrol.

DESCRIPTION OF ILLUSTRATIVE EMBODIMENTS

Figure 1:
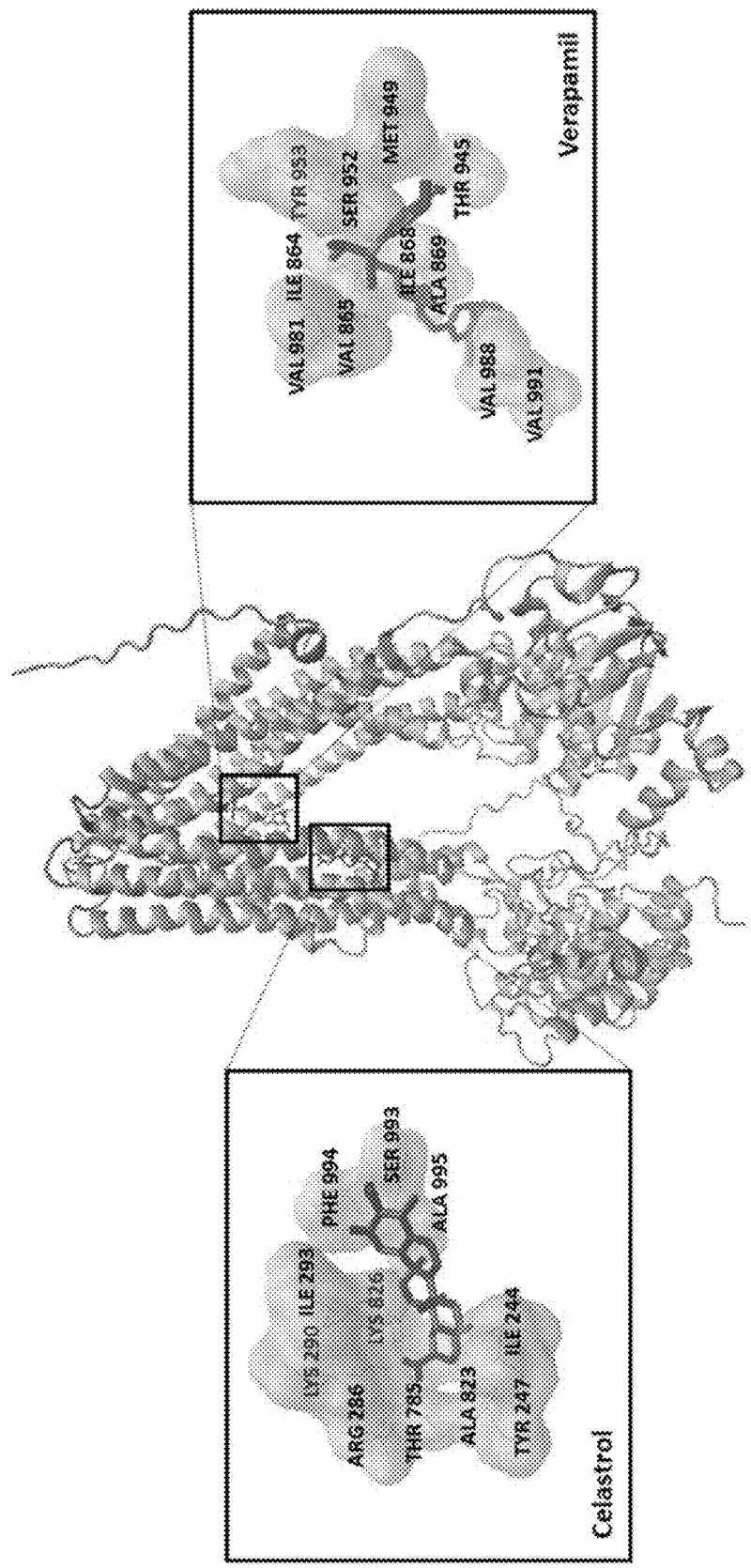
FIG. 1 is a 3D computational docking predicting with a docking calculation on the binding site and target region of celastrol (compound of Formula (IIIb)) on the P-glycoprotein efflux pump. Verapamil is the known P-glycoprotein inhibitor and applied as control to show its drug binding site on P-glycoprotein.
Figure 2A:
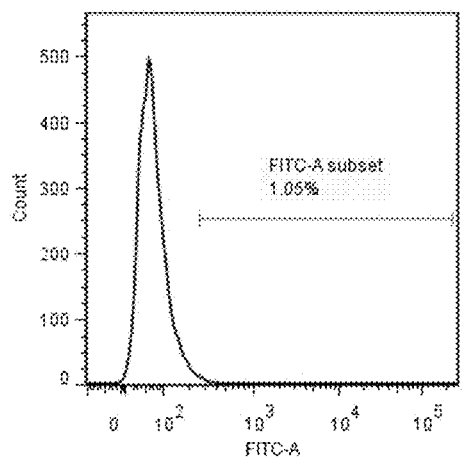
FIG. 2A to FIG. 2G show curves obtained with flow cytometry analysis of a Rho123 efflux assay in A549 taxol-resistant lung cancer cells. These cancer cells were treated with Rho123 dye in the presence of the P-glycoprotein inhibitor verapamil (10 μM) or celastrol with 0.1, 0.2, 0.5 and 1 μM compared to Rho123 control and an unstained group.
Figure 2B:
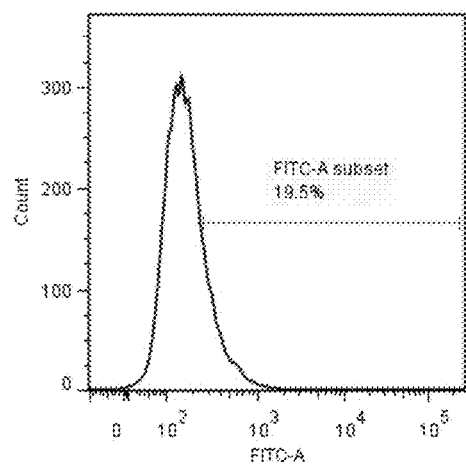
Figure 2C:
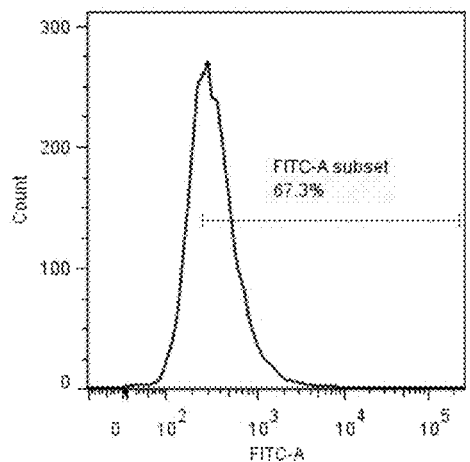
Figure 2D:
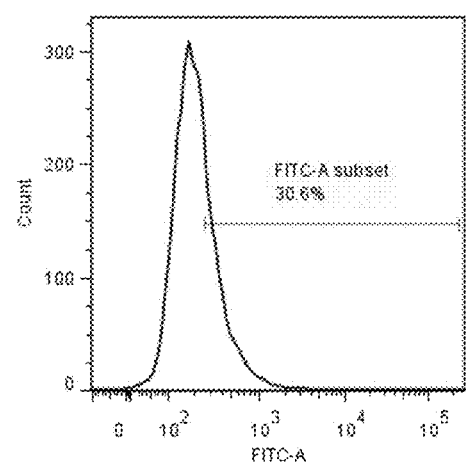
Figure 2E:
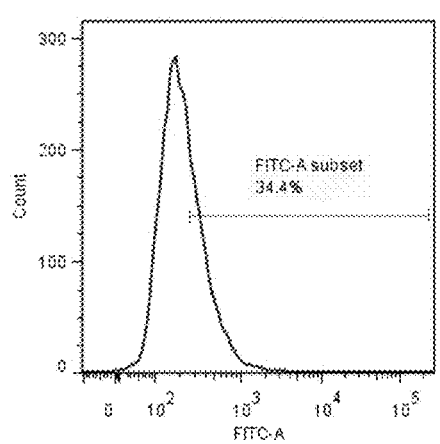
Figure 2F:
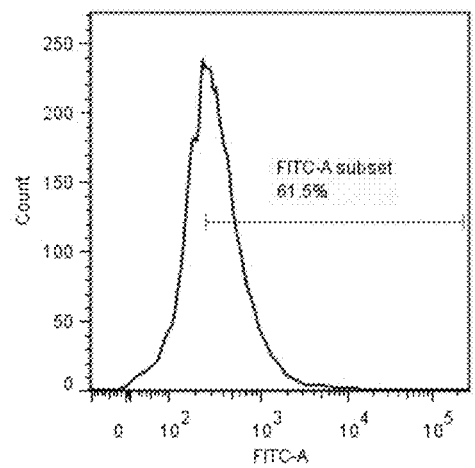
Figure 2G:
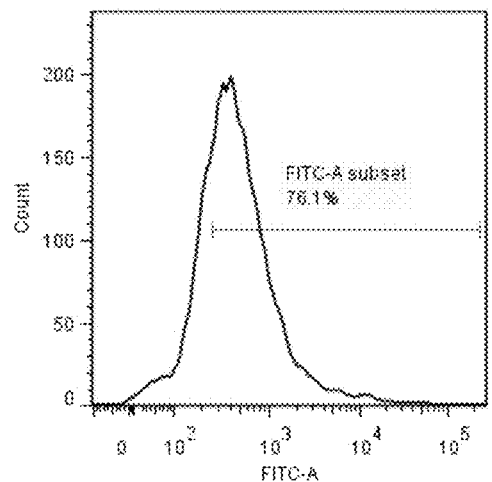
Figure 2H:
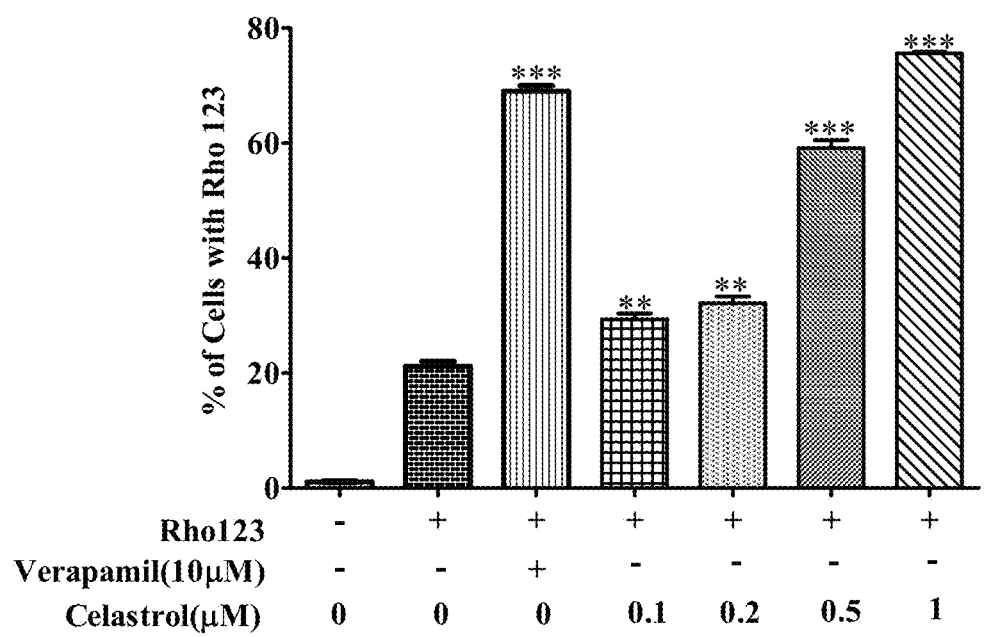
FIG. 2H is a bar chart showing the percentage of cells with Rho123 in verapamil or celastrol-treated A549 taxol-resistant lung cancer cells compared to Rho123 control and an unstained group.

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

The present invention relates in a first aspect to a method for treating a subject suffering from a multidrug-resistant cancer, i.e. a cancer with multidrug-resistant phenotype. Said method of treating multidrug-resistant cancer comprises the step of administering an effective amount of a quinonemethide triterpenoid to said subject. The quinonemethide triterpenoid can be a synthetic one or obtained from extracts of respective plants, in particular a quinonemethide triterpenoid obtained from plants of the family Celastraceae, in particular from plants of the genus *Celastrus, Catha, Maytenus, Salacia* and/or *Tripterygium*, more preferably from plants of the genus *Celastrus* and/or *Tripterygium*.

The term quinonemethide triterpenoid generally refers to a subclass of pentacyclic triterpenoids derived from the oleanane basic structure. The quinonemethide triterpenoid of the present invention has a structure of Formula (I) including any salt, solvate or anhydrate thereof:

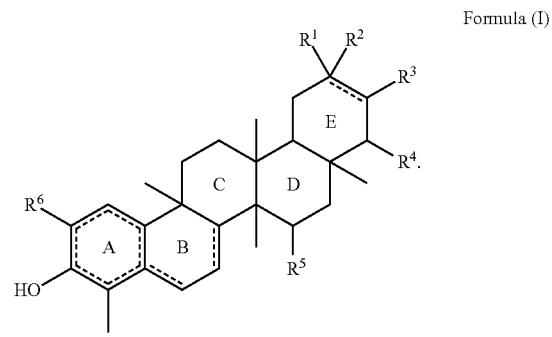

Formula (I)

$R^1$ is selected from —$CH_3$, —$CH_2OH$, —OH or —H. Preferably, $R^1$ is selected from —$CH_3$ or —$CH_2OH$.

$R^2$ is selected from —$CH_3$, —$CH_2OH$, —OH, —COOH, —$COOCH_3$, =$CH_2$ or —H. Preferably, $R^2$ is selected from —COOH or —$COOCH_3$.

$R^3$ is selected from —OH, =O or —H.

$R^4$ is selected from —OH or —H.

$R^5$ is selected from —OH or —H.

$R^6$ is selected from —OH or =O.

And wherein ═══ represents a single or double bond. I.e. ring A of the quinonemethide triterpenoid may have one, two or the maximum number of three double bonds forming an aromatic system. Additionally, in rings B and E there could be a further double bond. It is evident for the skilled person that the number and formal location of double bonds in ring A depends on the kind of $R^6$, namely whether $R^6$ is —OH or =O. Presence of the optional further double bond in ring B depends on the number and formal location of double bonds in ring A, which is evident for the skilled person, too.

Preferably, ring A has the maximum possible number of double bonds, i.e. two double bonds when $R^6$ is =O and three double bonds when $R^6$ is —OH. I.e. in one embodiment of the present invention, the quinonemethide triterpenoid has a structure of Formula (Ia):

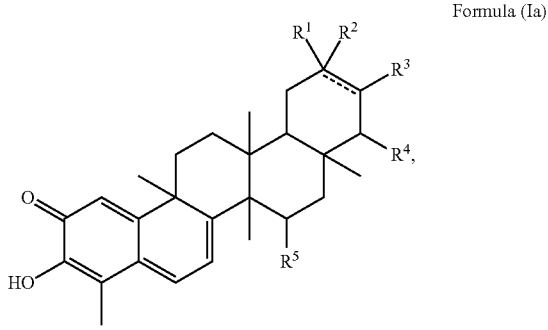

Formula (Ia)

wherein $R^1$ to $R^5$ and ═══ in Ring E are as defined above.

In another embodiment of the present invention, the quinonemethide triterpenoid has a structure of Formula (Ib):

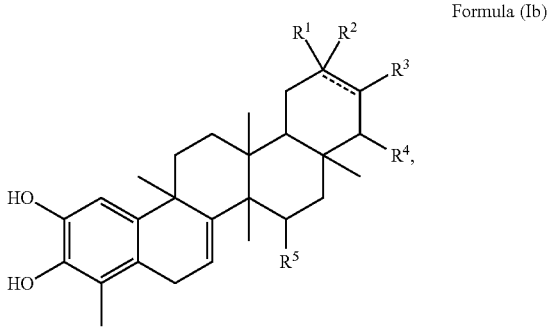

Formula (Ib)

wherein $R^1$ to $R^5$ and ═══ in Ring E are as defined above.

Also contemplated by the present invention are any pharmaceutically acceptable salts, hydrates, solvates, anhydrates as well as enantiomers and their mixtures, stereoisomeric forms, racemates, diastereomers and their mixtures of the quinonemethide triterpenoid of the present invention.

As used herein, the term "solvate" refers to a complex of variable stoichiometry formed by a solute, i.e. the quinonemethide triterpenoid, and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms stereoisomers, diastereomers, enantiomers and racemates are known to the skilled person.

Preferably, the quinonemethide triterpenoid of the present invention has a structure of Formula (II):

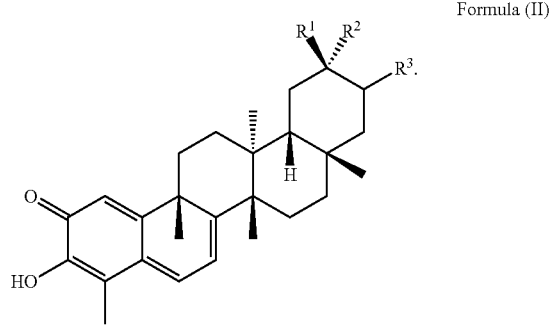

Formula (II)

$R^1$ is selected from —CH$_3$ or —CH$_2$OH, more preferably $R^1$ is —CH$_3$. $R^2$ is selected from —COOH or —COOCH$_3$, more preferably $R^2$ is —COOH. $R^3$ is selected from —OH, =O or —H, more preferably $R^3$ is —H.

In a further preferred embodiment of the present invention, the quinonemethide triterpenoid of the present invention has a structure of Formula (IIIa):

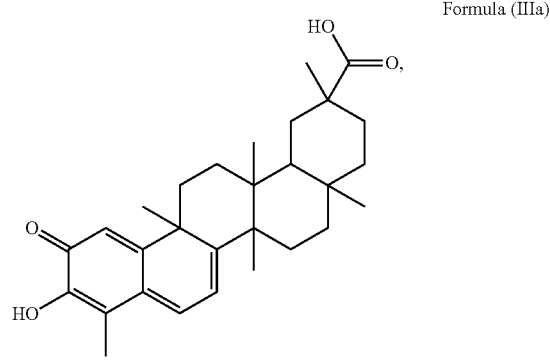 [SMILES: CC1=C(O)C(=O)C=C2C1=CC=C1C2(C)CCC2(C)C3CC(C)(C(=O)O)CCC3(C)CCC12C]

Formula (IIIa)

including any salt, solvate or anhydrate thereof and including any stereoisomer, diastereomer, enantiomer or racemate thereof.

In particular, the quinonemethide triterpenoid has a structure of Formula (IIIb):

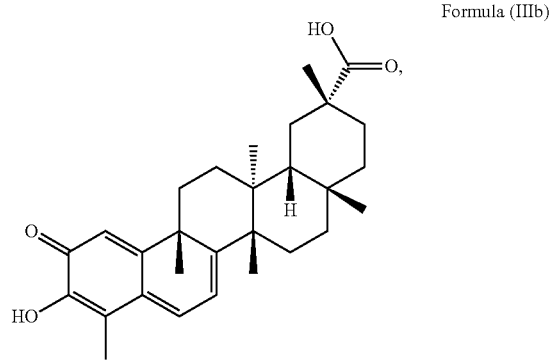

Formula (IIIb)

including any salt, solvate or anhydrate thereof. Said compound of Formula (IIIb) is known as celastrol, commercially available and can be prepared according to methods known to the skilled person or isolated, in particular, from *Tripterygium Wilfordii* (Thunder of God vine) and *Celastrus Regelii*.

In another embodiment of the present invention, the quinonemethide triterpenoid can have a structure of Formula (IV):

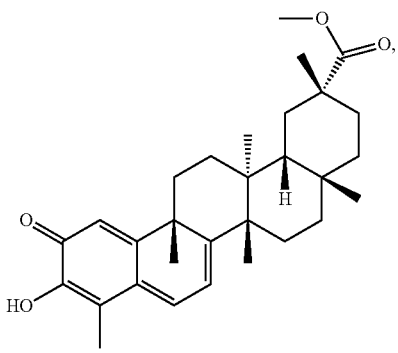

Formula (IV)

which is also known as pristimerin and, for example, commercially available.

In still other embodiments of the present invention, the quinonemethide triterpenoid of the present invention can have a structure of Formula (V):

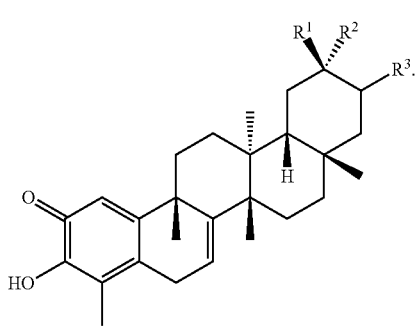

Formula (V)

$R^1$ is selected from —$CH_3$ or —$CH_2OH$, more preferably $R^1$ is —$CH_3$. $R^2$ is selected from —COOH or —$COOCH_3$, more preferably $R^2$ is —COOH. $R^3$ is selected from —OH, =O or —H, more preferably $R^3$ is —H. For example, the quinonemethide triterpenoid may have a structure of Formula (VI):

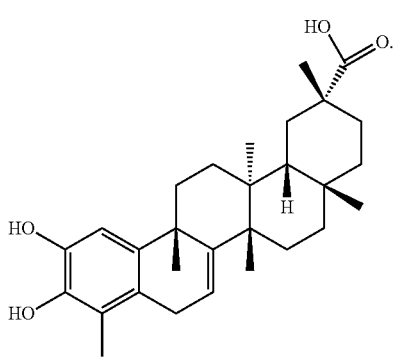

Formula (VI)

Compound of Formula (VI) is also known as dihydrocelastrol and, for example, obtainable by easily reducing celastrol such as with sodium borohydride and is also commercially available.

The expression "effective amount" and "effective dose" generally denote an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells.

The effective amount of the quinonemethide triterpenoid of the present invention may depend on the species, body weight, age and individual conditions of the subject and can be determined by standard procedures such as with cell cultures or experimental animals. A concentration of the quinonemethide triterpenoid such as the quinonemethide triterpenoid of Formula (II) in particular of Formula (IIIa) or (IIIb) for treating the subject may, for example, be at least 0.1 μM, preferably at least 0.2 μM, in particular at least 0.5 μM. The quinonemethide triterpenoid is preferably administered for at least 12 h, preferably at least 24 h, more preferably at least 48 h and in particular at least 72 h.

The subject can be a human or animal, in particular the subject is a mammal, preferably a human. The subject is, thus, preferably a human having a cancer with a multidrug-resistance. Said subject, thus, includes human subjects having a drug resistance to conventional therapeutic agents which induce cell death in cancer cells, i.e. which are used to treat cancer.

The terms "cancer" and "cancerous" refer to or describe a physiological condition in subjects in which a population of cells are characterized by unregulated cell growth. The term "tumor" simply refers to a mass being of benign (generally harmless) or malignant (cancerous) growth.

The multidrug-resistant cancer can be a multidrug-resistant cancer of any origin, in particular human origin. In particular, the multidrug-resistant cancer is selected from the group consisting of multidrug-resistant:
leukemia,
lymphoma,
kidney cancer and renal carcinoma, respectively,
pancreatic cancer,
ovarian cancer,
liver cancer,
myeloma,
sarcoma,
lung cancer,
breast cancer
gastric cancer, and
colon cancer.

Preferably, the cancer is selected from multidrug-resistant:
lung cancer
breast cancer
ovarian cancer
gastric cancer
renal carcinoma, or
colon cancer.

Still more preferably, the cancer is selected from multidrug-resistant:
lung cancer
ovarian cancer
breast cancer, or
colon cancer.

The provided method is used and particularly effective in treating subjects whose cancer has become "multidrug-resistant". The term "multidrug-resistance" is generally used for an acquired or natural, i.e. intrinsic, resistance of a cancer or more specifically of a cancer having cancer cells being simultaneously resistant to a range of chemotherapeutic compounds that usually differ structurally and functionally. Multidrug-resistant cancer with acquired drug resistance is characterized by a resumption of its growth and/or reappearance after having seemingly gone into remission, despite the administration of increased doses of a chemotherapeutic compound.

Cancers with cancer cells that have developed resistance to or are naturally resistant to two or more chemotherapeutic compounds are said to be "multidrug-resistant" in the present patent application such as to chemotherapeutic compounds selected from the group consisting of topoisomerase-II inhibitors, anthracyclines, coordination complexes of platinum, taxanes, protein kinase inhibitors, vinca alkaloids or derivatives thereof, topoisomerase-I inhibitors and nucleotide analogs or precursor analogs. Usually, a multidrug-resistant cancer is a cancer with cancer cells being resistant against three or more, five or more or even ten or more chemotherapeutic compounds such as those mentioned above. In preferred embodiments of the present invention, the multidrug-resistant cancer is a cancer having multidrug-resistant cancer cells, i.e. cancer cells which have developed resistance to or are naturally resistant to two or more chemotherapeutic compounds, wherein said multidrug-resistant cancer cells are resistant against at least one of paclitaxel (taxol), doxorubicin, cisplatin, etoposide and staurosporine, in particular against one of taxol or doxorubicin or both of them, more preferably against taxol.

A cancer is multidrug-resistant if it comprises cancer cells which are multidrug-resistant, in particular if more than 30% of cancer cells, more preferably more than 50% of cancer cells in said cancer are multidrug-resistant. Accordingly, the cancer cells with multidrug-resistant phenotype will show less sensitive or more tolerant to most common chemotherapeutic agents. In practice, this can be determined by taking a sample of the cancer and determining the percentage of cancer cells with multidrug-resistance.

A multidrug-resistance can be detected in a subject, cancer, tissue, or cell by administering to the subject, tissue, or cell, compounds such as chemotherapeutic compounds and determining the activity of the chemotherapeutic compounds such as the induction of cell death or the inhibition of the proliferation of cancer cells compared to a reference control, namely cells or tissue of the same cell or tissue type, a cancer or a subject that do not have multidrug-resistance or non-cancerous cells.

The multidrug-resistance according to the present invention is in particular at least one of:

ABC-protein dependent, i.e. mediated by ABC transporter proteins (hereinafter "ABC-proteins") such as by P-glycoprotein, i.e. is associated with an enhanced expression and/or enhanced functional activity of at least one ABC-protein in the multidrug-resistant cancer cells, in particular of P-glycoprotein, and/or apoptosis-deficient, i.e. associated with a decreased expression of at least one pro-apoptotic protein including gene knockout and/or decreased pro-apoptotic activity of at least one pro-apoptotic protein and/or enhanced expression of at least one anti-apoptotic protein and/or enhanced anti-apoptotic activity of at least one anti-apoptotic protein in the multidrug-resistant cancer cells; in particular apoptosis-deficient refers to at least one of p53-deficient, Bax-deficient or Bak-deficient.

In one embodiment of the present invention, the multidrug-resistance and hence the multidrug-resistant cancer is ABC-protein dependent, in particular P-glycoprotein dependent. In another embodiment of the present invention, the multidrug-resistance and, hence, the cancer is apoptosis-deficient, in particular at least one of p53-deficient, Bax-deficient or Bak-deficient.

ABC-proteins are transporter proteins that may act to remove chemotherapeutic compounds from cells. The thus, resulting multidrug-resistant phenotype can be specifically detected in a subject, tissue, cancer or cell by administering to the subject, tissue, or cell, a compound such as a chemotherapeutic compound which is transported by the ABC-proteins, i.e. is a substrate to ABC-proteins such as to P-glycoprotein. The method then encompasses determining the amount of said chemotherapeutic compound in the cells compared with the amount in a reference control, i.e. a subject, a tissue, cancer or a cell of the same cell or tissue type that does not express said multidrug-resistance phenotype, namely with ABC-protein expression as present in non-cancerous cells, in particular cancer cells or tissue without the multidrug-resistance phenotype or non-cancerous cells or tissue.

Said ABC-protein is in particular selected from the "B" subfamily, "C" subfamily or "G" subfamily of ABC-proteins. Most preferably, said ABC-protein is P-glycoprotein, i.e. in embodiments of the present invention, the multidrug-resistant cancer is a P-glycoprotein-dependent multidrug-resistant cancer. Preferred "B" subfamily members include the protein encoded by ABCB1 (MDR1), ABCB4 (MDR2), ABCB5 or ABCB11 in humans or corresponding genes in other mammals. Preferred "C" subfamily members include the protein encoded by ABCC1 (MRP1) in humans or corresponding genes in other mammals. Preferred "G" subfamily members include the protein encoded by ABCG2 (BCRP) in humans or corresponding genes in other mammals. More preferably, the ABC-protein is of the "B" subfamily, in particular the ABC-protein is the protein encoded by ABCB1, ABCB4, ABCB5 or ABCB11 in humans or corresponding genes in other mammals which can transport drugs, in particular ABCB1 and/or ABCB5, most preferably ABCB1 or corresponding genes in other mammals, i.e. most preferably P-glycoprotein.

P-glycoprotein as used herein refers to the protein as encoded by the ABCB1 (MDR1) gene in humans or respective genes including SNPs and naturally occurring mutations to said gene and as encoded by corresponding genes in other mammals, respectively.

An enhanced expression and/or enhanced functional activity of at least one ABC-protein, i.e. ABC-protein-dependent multidrug-resistant cancer, means an expression and/or functional activity exceeding, in particular significantly exceeding, the one in normal cells or tissue, i.e. non-cancerous cells or tissue, or cancer cells without the multidrug-resistant phenotype. The term "enhanced expression" or "enhanced functional activity" of at least one ABC-protein such as P-glycoprotein includes embodiments in which the multidrug-resistant cancer cells express the ABC-protein such as P-glycoprotein, whereas in the reference control, i.e. cancer cells without the multidrug-resistant phenotype or non-cancerous cells of the same cell or tissue type, said ABC-protein such as P-glycoprotein is not expressed, at all. I.e. when said reference control does not express the ABC-protein such as P-glycoprotein, multidrug-resistant cancer cells having a detectable expression or functional activity of the ABC-protein such as P-glycoprotein are ABC-protein-dependent such as P-glycoprotein-dependent by definition.

Whether a multidrug-resistant cancer is an ABC-protein-dependent such as P-glycoprotein-dependent multidrug-resistant cancer can be determined by methods known to the skilled person in particular comprising immunological methods accompanied by the use of MDR-specific antibodies, immunocytochemistry and immunohistochemistry, respectively, by determining respective mRNA levels such as with Northern blots or quantitative RT-PCR, with MDR-specific antibodies in vivo or with an ABC-protein such as P-glycoprotein efflux assay detecting the efflux of a marker.

In particular, an ABC-protein such as P-glycoprotein efflux assay can be used for determining the functional activity of ABC-proteins, i.e. for determining whether multidrug-resistant cancer cells are ABC-protein-dependent. Markers which can be used in said efflux assay include drugs which are a substrate for the respective ABC-protein, a radionuclide or a dye like a fluorescent dye selected from Rhodamine123 (also referenced as "Rho123", 6-amino-9-(2-methoxycarbonylphenyl) xanthen-3-ylidene]azanium chloride), DiOC2 (3,3'-diethyloxacarbocyanine iodide) or Calcein AM (calcein o,o'-diacetate tetrakis(acetoxymethyl) ester). The cells to be analyzed are usually incubated with the marker at physiological conditions, i.e. in particular at about 37° C. for at least 20 min, in particular for at least 30 min and especially for about 1 h. Usually, the cells are washed subsequently at least 1-time, in particular more than 1-time preferably with a buffer, in particular 5-times with ice-cold Phosphate-buffered saline (PBS). Elimination from or, alternatively, retention of the marker in the multidrug-resistant cells can be determined and compared with a reference control, i.e. cells with ABC-protein expression as present in non-cancerous cells such as cancer cells that do not have a multidrug-resistance phenotype or non-cancerous cells of the same cell or tissue type. For example, fluorescence of a fluorescent marker can be determined by flow cytometry.

Preferably, an ABC-protein-dependent such as a P-glycoprotein-dependent multidrug-resistant cancer is a cancer comprising multidrug-resistant cancer cells with an expression of ABC-protein or ABC-protein functional activity exceeding the one in the reference control by at least 10%, in particular by at least 20%. For example, the expression or functional activity of P-glycoprotein in P-glycoprotein-dependent multidrug-resistant cancer cells is at least 10% or at least 20% higher than the expression or functional activity of P-glycoprotein in the reference control.

In particular embodiments of the present invention, an ABC-protein efflux assay is carried out to determine whether a multidrug-resistant cancer is ABC-protein-dependent. Thereby, the amount of marker, in particular a fluorescent dye, taken up by a multidrug-resistant cancer cell or a sample with such cancer cells is compared with the amount taken up by a reference control, namely cells with ABC-protein expression as present in non-cancerous cells, such as cancer cells that do not have a multidrug-resistance phenotype or non-cancerous cells of the same cell or tissue type. The multidrug-resistant cancer cells or the sample of multidrug-resistant cancer cells and, thus, the cancer is preferably considered for being ABC-protein-dependent according to the present invention, if the multidrug-resistant cancer cells have a reduced amount of marker such as dye, in particular an at least 50%, and more preferably at least 60% reduced amount of marker in the cells compared to the amount of marker in the reference control as revealed by the efflux assay or, alternatively, if the sample of multidrug-resistant cancer cells has a reduced percentage of cells with marker, namely an at least 50 percentage points and in particular at least 60 percentage points reduced percentage of cells with marker after carrying out the efflux assay compared to the reference control. In particular, a sample of multidrug-resistant cancer cells and, thus, a cancer having those cells, is preferably considered for being P-glycoprotein-dependent, if it comprises less cells with marker such as dye like Rho123 as revealed by the P-glycoprotein efflux assay compared to the reference control which is a cell sample with P-glycoprotein expression as present in cancer cells that do not have a multidrug-resistance phenotype or non-cancerous cells of the same cell or tissue type. Namely, the percentage of cells with marker is preferably at least 50 percentage points, more preferably at least 60 percentage points and in particular at least 70 percentage points lower than the percentage of cells with marker in the reference control as revealed by the P-glycoprotein efflux assay.

The multidrug-resistant cancer is an embodiment of the present invention a cancer comprising multidrug-resistant P-glycoprotein-dependent cancer cells, i.e. multidrug-resistant cancer cells having an enhanced expression of P-glycoprotein and/or an enhanced functional activity of P-glycoprotein, in particular comprising more than 30% of said cancer cells, more preferably more than 50% of said cancer cells.

The term "apoptosis-deficient" used herein refers to a cancer having at least one of (i) decreased expression including gene knockout and/or decreased pro-apoptotic activity of at least one pro-apoptotic protein or (ii) enhanced expression and/or enhanced anti-apoptotic activity of at least one anti-apoptotic protein or both of them, i.e. (i) and (ii). Pro- and/or anti-apoptotic proteins in particular include p53, mitogen-activated protein kinase (MAPK)-family members and B cell lymphoma 2 (Bcl-2) family members.

Whether a multidrug-resistant cancer is apoptosis-deficient can be determined by methods known to the skilled person, namely by measuring the expression of the pro-apoptotic protein and/or anti-apoptotic protein and/or by determining the apoptotic activity of the pro-apoptotic protein and/or the anti-apoptotic protein compared with a reference control, namely cancer cells that do not have a multidrug-resistance phenotype or non-cancerous cells of the same cell or tissue type. Suitable methods for determining the expression may include immunological methods accompanied by the use of specific antibodies, immunocytochemistry and immunohistochemistry, respectively, or by determining respective mRNA levels such as with Northern blots or quantitative RT-PCR. The apoptotic activity can be determined by assays which determine the rate of apoptosis known to the skilled person such as assays determining cytomorphological alterations, DNA fragmentation such as by TUNEL assay along with flow cytometry, detection of apoptosis pathway downstream targets, cleaved substrates, regulators and inhibitors, membrane alterations, or mitochondrial assays. The apoptotic activity is in particular determined with a TUNEL assay along with flow cytometry or other commercially available apoptosis assays and kits after induced DNA damage such as 12 h to 48 h after irradiation of the multidrug-resistant cancer cells and of the reference control such as with γ-irradiation with a 5-10 Gy dose or UV-radiation like UVB radiation with 100-250 J/m$^2$. As one of skill in the art will appreciate, any suitable means of detecting apoptosis may be used in the method of the invention.

Anti-apoptotic proteins are proteins which prevent cell apoptosis. The at least one anti-apoptotic protein is preferably selected from the Bcl-2-family, namely Bcl-2, Bcl-$X_L$, Bcl-w, Bcl-2A1 or Mcl-1, in particular the anti-apoptotic protein is Bcl-2. Enhanced expression and/or enhanced anti-apoptotic activity of the anti-apoptotic protein in particular means an expression and/or anti-apoptotic activity of said at least one protein which is increased by at least 5%, more preferably at least 10% and most preferably by more than 50% compared with a reference control, namely cancer cells without the multidrug-resistant phenotype or non-cancerous cells of the same cell or tissue type. Enhanced expression and/or enhanced anti-apoptotic activity of the anti-apoptotic protein may be caused, for example, by an increased expression of anti-apoptotic wild-type protein or and/or an expression of an anti-apoptotic mutant protein having increased anti-apoptotic activity. A mutant anti-apoptotic protein has an amino acid sequence different from the wild-type protein expressed in healthy cells without a mutation in the respective encoding genes.

Pro-apoptotic proteins are proteins which induce and in particular initiate the cell apoptosis pathway. In particular, pro-apoptotic proteins are selected from at least one of p53 protein and pro-apoptotic proteins of the Bcl-2-family. The term "p53 protein" used herein includes respective p53 isoforms encoded by the TP53 gene such as p53α, p53β, p53γ, Δ40p53α, Δ40p53β, Δ40p53γ, Δ133p53α, Δ133p53β, Δ133p53γ, Δ160p53α, Δ160p53β, Δ160p53γ and the like. Pro-apoptotic proteins of the Bcl-2-family are preferably selected from at least one of Bax, Bak, Bad, Bik, Bim, PUMA, NOXA, Bok, Bnip3, Bmf, Hrk and Bid, in particular of at least one of Bax or Bak. Most preferably, the pro-apoptotic protein is selected from at least one of p53, Bax or Bak, also referenced as p53-, Bax- or Bak-deficient multidrug-resistant cancer cells and cancer, respectively. Decreased expression and/or decreased pro-apoptotic activity of pro-apoptotic proteins in particular means an expression and/or pro-apoptotic activity of said at least one protein which is decreased by at least 5%, more preferably by at least 10% and most preferably by more than 50% compared with a reference control, namely cancer cells without the multidrug-resistant phenotype or non-cancerous cells of the same cell or tissue type. In particular embodiments of the present invention, said at least one pro-apoptotic protein is not detectably expressed in the multidrug-resistant cancer cells. Decreased expression used herein in particular also includes "gene knockout", which term is used herein for embodiments in which the respective gene(s) expressing the pro-apoptotic protein(s) is/are inoperative, in particular made inoperative by common genetic techniques known to the skilled person such that the cell or subject preferably carries no functional gene copy, i.e. the respective pro-apoptotic protein(s) is/are preferably not expressed in the cell, cancer or subject, at all. Decreased expression and/or decreased pro-apoptotic activity of at least one pro-apoptotic protein may be caused by, for example, a decreased expression of pro-apoptotic wild-type protein and/or by an expression of a pro-apoptotic mutant protein with decreased pro-apoptotic activity and/or by a gene knockout. A mutant pro-apoptotic protein has an amino acid sequence different from the wild-type protein expressed in healthy cells without a mutation in the respective encoding genes.

The multidrug-resistant cancer in one embodiment of the present invention is a cancer comprising multidrug-resistant apoptosis-deficient cancer cells, in particular comprising more than 30% of said cancer cells, more preferably more than 50% of said cancer cells. The multidrug-resistant cancer is, thus, in embodiments an apoptosis-deficient multidrug-resistant cancer. In embodiments of the present invention, the apoptosis-deficient cancer is a cancer having cancer cells with enhanced expression and/or enhanced anti-apoptotic activity of Bcl-2 and/or decreased expression including gene knockout and/or decreased pro-apoptotic activity of at least one of p53, Bax or Bak.

Most preferably, the apoptosis-deficient cancer is a cancer having cancer cells with a decreased expression including gene knockout and/or decreased pro-apoptotic activity of at least one pro-apoptotic protein selected from at least one of p53, Bax or Bak, which is also referenced herein as "p53 deficient", "Bak-deficient" or "Bax-deficient" cancer cells and cancer, respectively. I.e. "p53 deficient", "Bak-deficient" or "Bax-deficient" means a decreased expression including gene knockout and/or decreased pro-apoptotic activity of p53, Bax and Bak, respectively. In further preferred embodiments, the apoptosis-deficient cancer is a cancer having cancer cells with a decreased expression including gene knockout of at least one pro-apoptotic protein selected from p53, Bax or Bak or a decreased expression including gene knockout of two or all of them. In a further embodiment, the apoptosis-deficient cancer is a cancer having cancer cells with a gene knockout of at least one pro-apoptotic protein selected from p53, Bax or Bak such as a gene knockout of two or all of them, in particular the cell, cancer or subject does not carry a functional gene copy of at least one of the respective encoding gene(s).

In an embodiment of the present invention, the multidrug-resistant cancer is a cancer comprising at least one of
  multidrug-resistant apoptosis-deficient cancer cells with a decreased expression including gene knockout and/or decreased pro-apoptotic activity of at least one of p53, Bax or Bak, and/or
  multidrug-resistant P-glycoprotein-dependent cancer cells,
in particular comprising more than 30% of said cancer cells, more preferably more than 50% of said cancer cells.

The quinonemethide triterpenoid is in preferred embodiments of the present invention administered in combination with an effective amount of at least one chemotherapeutic compound. As used herein, the term "chemotherapeutic compound" includes drugs which are advantageously and commonly administered to cancer or cancer cells without the multidrug-resistance phenotype, i.e. which have been known to affect cancer cells.

In particular, the chemotherapeutic compound is a substrate for P-glycoprotein. The chemotherapeutic compound is preferably selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog. Such chemotherapeutic compounds include etoposide, doxorubicin, daunorubicin, cisplatin, paclitaxel (taxol), docetaxel, staurosporine, vinblastine, vincristine, topotecan and methotrexate. Preferably, the chemotherapeutic compound is selected from the group consisting of cisplatin, doxorubicin, taxol, etoposide and staurosporine. Still more preferably, the chemotherapeutic compound is taxol, also named paclitaxel, or is doxorubicin. Most preferably, the chemotherapeutic compound used in combination with the quinonemethide triterpenoid of the present invention is taxol. Further chemotherapeutic compounds which are substrates for the P-glycoprotein efflux can be used in combination with the quinonemethide triterpenoid of the present invention, too.

In especially preferred embodiments of the present invention, the quinonemethide triterpenoid has the structure of Formula (IIIa) or (IIIb):

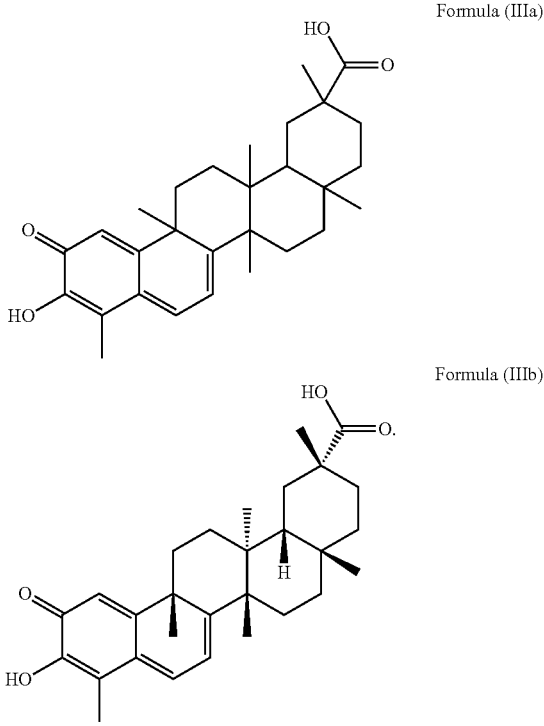

and the chemotherapeutic compound is taxol.

The chemotherapeutic compound can be administered before, after or simultaneously with the quinonemethide triterpenoid, in particular before or simultaneously with the quinonemethide triterpenoid, further preferred simultaneously with the quinonemethide triterpenoid.

The method of the present invention may comprise further steps before administering the compound of Formula (I), in particular the quinonemethide triterpenoid of Formula (II), (IIIa) or (IIIb) of
obtaining a sample, in particular cancer cells, from the subject;
testing said sample for at least one of
the expression of at least one ABC-protein, in particular of P-glycoprotein;
at least one ABC-protein, in particular the P-glycoprotein, functional activity;
the expression of at least one pro- or anti-apoptotic protein, in particular selected from at least one of p53, Bax or Bak;
the apoptotic activity of at least one pro- or anti-apoptotic protein, in particular selected from at least one of p53, Bax or Bak;
optionally correlating the expression and/or functional activity of the at least one ABC-protein, in particular of P-glycoprotein, and/or the expression or activity of the at least one pro- or anti-apoptotic protein with an outcome and if conditions are met, administrating the quinonemethide triterpenoid of the present invention, in particular the quinonemethide triterpenoid of Formula (II), (IIIa) or (IIIb), to said subject; alone or in combination with a chemotherapeutic compound.

The skilled person is aware of methods for determining the expression of P-glycoprotein such as an antibody assay or its functional activity such as with an efflux assay as well as methods for determining the expression or apoptotic activity of pro- or anti-apoptotic proteins.

According to the invention is also the quinonemethide triterpenoid of the present invention, in particular of Formula (II), (IIIa) or (IIIb), for use as a medicament for the treatment of multidrug-resistant cancer, in particular P-glycoprotein dependent multidrug-resistant cancer or one of p53-, Bax- or Bak-deficient multidrug-resistant cancer. The quinonemethide triterpenoid of the present invention, in particular of Formula (II), (IIIa) or (IIIb), can be used in an effective amount for treating an animal or a human, in particular a mammal, preferably a human. Another aspect of the invention refers to the use of the quinonemethide triterpenoid of the present invention, in particular of Formula (II), (IIIa) or (IIIb), for preparing a medicament for treatment of multidrug-resistant cancer, in particular P-glycoprotein-dependent cancer or one of p53-, Bax- or Bak-deficient multidrug-resistant cancer. The quinonemethide triterpenoid of the present invention, in particular of Formula (II), (IIIa) or (IIIb), may be used in combination with at least a further therapeutic compound, preferably therapeutic compounds which are used for treating cancer such as chemotherapeutic compounds.

The present invention also relates to a method of using the quinonemethide triterpenoid of the present invention, in particular of Formula (II), (IIIa) or (IIIb), as P-glycoprotein efflux pump inhibitor for treating multidrug-resistant cancer comprising applying an effective amount of said compound for inhibiting P-glycoprotein by direct binding and inhibition, thereby in particular producing and allowing for collateral sensitivity in multidrug-resistant cancers.

The inhibition of P-glycoprotein can be determined with a P-glycoprotein efflux assay by determining the amount of multidrug-resistant cancer cells in a sample with marker such as with Rho123 in the presence of the quinonemethide triterpenoid of the present invention after carrying out the efflux assay compared to a reference control with multidrug-resistant cancer cells in the absence of the quinonemethide triterpenoid. In particular, the percentage of cells with marker such as Rho123 is at least 15, further preferably at least 20, more preferably at least 30 and in particular at least 40 percentage points and more preferably more than 50 percentage points increased compared to the reference control by the quinonemethide triterpenoid of the present invention. Usually, the multidrug-resistant cancer cells are contacted with the quinonemethide triterpenoid and incubated for at least 12 h, in particular for about 24 h at about 37° C. The reference control is, instead, not incubated with the quinonemethide triterpenoid. Usually, the marker in particular Rho123 is subsequently added while further incubating at about 37° C. for at least 20 min, preferably for at least 30 min and in particular for about 1 h.

In another aspect of the present invention, the invention provides a method for specifically targeting cancer cells with multidrug-resistance, in particular ABC protein-dependent such as P-glycoprotein dependent multidrug-resistant cancer cells or apoptosis-deficient such as p53-, Bax- and/or Bak-deficient multidrug-resistant cancer cells. Said method comprises the step of contacting a population of cancer cells with multidrug-resistance with the quinonemethide triterpenoid described above or a salt, solvate or anhydrate thereof. Preferably, the growth of the multidrug-resistant cancer cells is suppressed or cell death is induced, in particular cell death is induced. Preferably, a MTT assay and annexin V flow cytometry analysis are used for measuring the effect on cell death and cell viability.

The multidrug-resistant cancer cells are in particular ABC-protein-dependent, most preferably P-glycoprotein-dependent and/or apoptosis-deficient such as p53-, Bax- or Bak-deficient. In one embodiment of the present invention, the multidrug-resistant cancer cells used within the method are P-glycoprotein-dependent multidrug-resistant cancer cells. In another embodiment of the present invention, the multidrug-resistant cancer cells used within the method are at least one of p53-deficient, Bax-deficient or Bak-deficient multidrug-resistant cancer cells.

The multidrug-resistant cancer cells can be of any origin, in particular human origin. In particular, the multidrug-resistant cancer cells are from a multidrug-resistant:
leukemia,
lymphoma,
kidney cancer and renal carcinoma, respectively,
pancreatic cancer,
ovarian cancer,
liver cancer,
myeloma,
sarcoma,
lung cancer,
breast cancer
gastric cancer, or
colon cancer.

More preferably, the multidrug-resistant cancer cells are from multidrug-resistant:
lung cancer
breast cancer
ovarian cancer
gastric cancer
renal carcinoma, or
colon cancer.

Most preferably, the multidrug-resistant cancer cells are from multidrug-resistant:
lung cancer
ovarian cancer
breast cancer, or
colon cancer.

In preferred embodiments of the present invention, the multidrug-resistant cancer cells are resistant against at least one of paclitaxel (taxol), doxorubicin, cisplatin, etoposide and staurosporine, in particular against one of taxol or doxorubicin or both of them, most preferably against taxol.

The concentration of the quinonemethide triterpenoid used for contacting the multidrug-resistant cancer cells may range from 0.1 μM to 100 μM, preferably from 0.1 μM to 20 μM, in particular from 0.1 μM to 10 μM, more preferably between 0.1 μM and 8 μM, i.e. between 0.1 μmol/l (=0.1 mmol/m$^3$) and 8 μmol/l (=8 mmol/m$^3$), such as 0.108 to 6.109 μM. The multidrug-resistant cancer cells are preferably contacted with the quinonemethide triterpenoid of the present invention for at least 12 h, preferably for at least 24 h, more preferably for at least 48 h and in particular for at least 72 h.

Preferably, the IC$_{50}$ of the quinonemethide triterpenoid towards the multidrug-resistant cancer cells is at most 10 μM, more preferably at most 5 μM and in particular at most 2 μM and further preferred at most 1 μM after about 72 h. The Resistant Factor of the quinonemethide triterpenoid of the present invention towards the multidrug-resistant cancer cells is preferably less than 0.98, more preferably less than 0.95 and in particular less than 0.85 and more preferably less than 0.7 or even lower than 0.65. The Resistant Factor is calculated by dividing the IC$_{50}$ of the quinonemethide triterpenoid towards multidrug-resistant cells by its IC$_{50}$ towards cancer cells of the same cell type or tissue which do not have a multidrug-resistance phenotype. A Resistant Factor <1 indicates that a compound is especially effective in multidrug-resistant cancer cells compared to cancer cells of the same cell type or tissue which do not have a multidrug-resistant phenotype, i.e. is especially suitable to specifically target multidrug-resistant cancer cells.

In one embodiment of the present invention, the multidrug-resistant cancer cells used within the method are P-glycoprotein-dependent multidrug-resistant cancer cells and the Resistant Factor of the quinonemethide triterpenoid of the present invention is at most 0.7, wherein the multidrug-resistant cancer cells are from a lung cancer, ovarian cancer, colon cancer or breast cancer and wherein the multidrug-resistant cancer cells are resistant against taxol. In another embodiment of the present invention, the multidrug-resistant cancer cells used within the method are P-glycoprotein-dependent multidrug-resistant cancer cells and the Resistant Factor of the quinonemethide triterpenoid of the present invention is at most 0.9, wherein the multidrug-resistant cancer cells are from a breast cancer or leukemia and wherein the multidrug-resistant cancer cells are resistant against doxorubicin. In a further embodiment of the present invention, the multidrug-resistant cancer cells used within the method are P-glycoprotein-dependent multidrug-resistant cancer cells and the Resistant Factor of the quinonemethide triterpenoid of the present invention is at most 0.95, wherein the multidrug-resistant cancer cells are from a gastric cancer and wherein the multidrug-resistant cancer cells are resistant against cisplatin. In still another embodiment of the present invention, the multidrug-resistant cancer cells used within the method are at least one of p53-deficient, Bax-deficient or Bak-deficient multidrug-resistant cancer cells and wherein the Resistant Factor of the quinonemethide triterpenoid of the present invention is at most 0.65 and wherein the multidrug-resistant cancer cells are from a colon cancer and wherein the multidrug-resistant cancer cells are resistant against taxol.

In especially preferred embodiments of the present invention, the quinonemethide triterpenoid used for contacting the cancer cells has a structure of Formula (IIIa) or (IIIb):

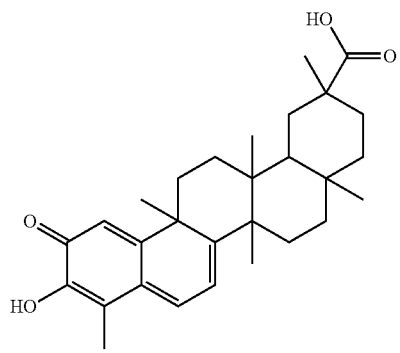

Formula (IIIa)

-continued

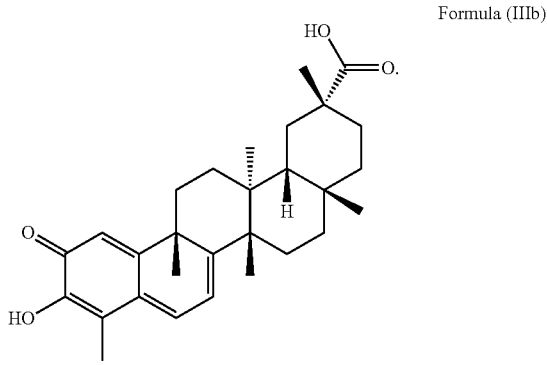

Formula (IIIb)

and the cancer cells are contacted with between 0.1 μM and 8 μM, more preferably between 0.108 μM and 6.109 μM of said quinonemethide triterpenoid.

The step of contacting the cancer cells with the quinonemethide triterpenoid of the present invention, in particular of Formula (II), (IIIa) or (IIIb), may be carried out by applying an incubation solution comprising the compound of Formula (I) such as of Formula (II), (IIIa) or (IIIb) to said cells which incubation solution may further comprise suitable excipients such as buffers or a suitable growth medium.

The method may further comprise contacting said cells with a further therapeutic compound, in particular a compound used for treating cancer such as a chemotherapeutic compound; including for example, cisplatin, doxorubicin, taxol, etoposide and staurosporine; before, at the same time with or subsequent to the application of the quinonemethide triterpenoid of the present invention. Preferably, the growth of the tumor cells is suppressed and/or cell death is induced. In particular, the quinonemethide triterpenoid of the present invention binds to and inhibits the P-glycoprotein activity in said cancer cells.

In a further aspect, the present invention refers to a method of potentiating the activity of a chemotherapeutic compound in multidrug-resistant cancer cells comprising contacting said cancer cells with
   a quinonemethide triterpenoid as described above; and
   a chemotherapeutic compound, wherein the chemotherapeutic compound is selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog,
   and wherein the multidrug-resistant cancer cells are resistant against the chemotherapeutic compound.

The quinonemethide triterpenoid of the present invention is effective for potentiating the activity of the chemotherapeutic compound, i.e. for increasing the effectiveness of the chemotherapeutic compound to inhibit proliferation of the multidrug-resistant cancer cells, inducing cell death of the multidrug-resistant cancer cells, and/or indirectly inhibiting development of the multidrug-resistant cancer cells. In particular, the activity of the chemotherapeutic compound to inhibit proliferation or inducing cell death, i.e. apoptosis, is increased. "Potentiating the activity" as used herein means any measurable increase such as of at least 5%, preferably of at least 10% and more preferably of at least 20%.

For example, potentiating the activity of a chemotherapeutic compound can be an increase with regard to cell death, in particular the percentage of total cell deaths after contacting the multidrug-resistant cancer cells with the chemotherapeutic compound and the quinonemethide triterpenoid preferably for at least 12 h, in particular for about 24 h, is at least 5, more preferably at least 10 and in particular at least 20, and further preferably at least 25 and still more preferably at least 40 percentage points and further preferred at least 60 percentage points increased compared to the percentage of cell deaths in multidrug-resistant cancer cells which have been contacted with the chemotherapeutic compound, but not with the quinonemethide triterpenoid. The percentage of total cell deaths and cell viability is preferably measured with a MTT assay and annexin V flow cytometry analysis.

In an embodiment of the present invention, potentiating the activity of a chemotherapeutic compound refers to a decrease in $IC_{50}$ of the chemotherapeutic compound towards the multidrug-resistant cells in the presence of the quinonemethide triterpenoid of the present invention compared to the $IC_{50}$ of the chemotherapeutic compound towards the multidrug-resistant cells in the absence of the quinonemethide triterpenoid. Preferably, the $IC_{50}$ of the chemotherapeutic compound towards the multidrug-resistant cells is at least 50%, more preferably at least 70% and in particular more than 80% and further preferred at least 90% reduced in the presence of the quinonemethide triterpenoid of the present invention.

The multidrug-resistant cancer cells are preferably contacted with from 0.1 μM to 10 μM of the quinonemethide triterpenoid, preferably from 0.1 μM to 5 μM, in particular from 0.1 μM to 2 μM, more preferably between 0.1 μM and 1 μM, i.e. between 0.1 μmol/l (=0.1 mmol/m³) and 1 μmol/l (=1 mmol/m³), in particular 0.5 μM. The cancer cells are preferably contacted with the quinonemethide triterpenoid for at least 12 h, preferably for about 24 h. The step of contacting the cells with the quinonemethide triterpenoid such as the quinonemethide triterpenoid of Formula (II), (IIIa) or (IIIb) and the chemotherapeutic compound may be carried out by applying at least one incubation solution comprising the quinonemethide triterpenoid and/or the chemotherapeutic compound to said cells which incubation solution may further comprise suitable excipients such as solvents, buffers or a suitable growth medium.

The multidrug-resistant cancer cells are contacted with the chemotherapeutic compound before, after or simultaneously with the quinonemethide triterpenoid, in particular before or simultaneously with the quinonemethide triterpenoid, more preferably simultaneously with the quinonemethide triterpenoid. The chemotherapeutic compound is preferably selected from cisplatin, doxorubicin, paclitaxel (taxol), etoposide or staurosporine, in particular from taxol or doxorubicin, more preferably from taxol. In most preferred embodiments, the cells are contacted with between 0.01 μM and 100 μM, more preferably with 40 μM taxol as chemotherapeutic compound.

Most preferably, the multidrug-resistant cancer cells are from a lung tumor and resistant against at least paclitaxel (taxol) and wherein the chemotherapeutic compound is taxol.

Preferably, the multidrug-resistant cancer cells are contacted with a quinonemethide triterpenoid having a structure of Formula (IIIa) or (IIIb):

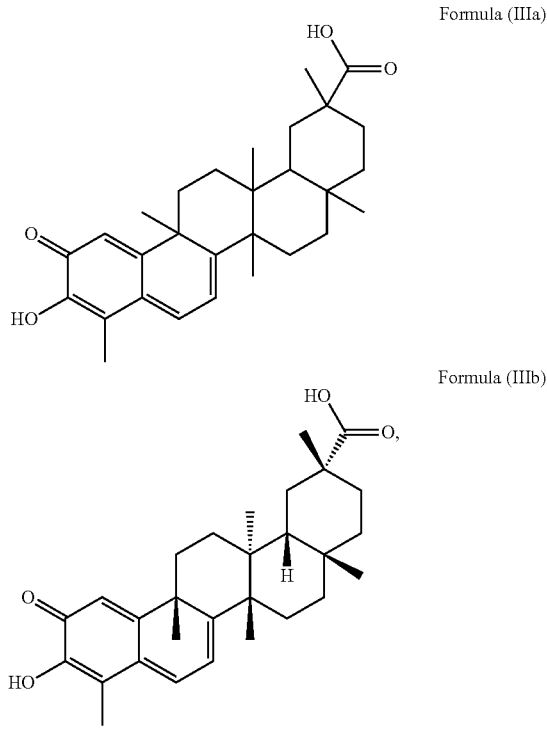

Formula (IIIa)

Formula (IIIb)

wherein the multidrug-resistant cancer cells are preferably contacted with between 0.1 µM and 1 µM of the quinonemethide triterpenoid.

Further in accordance with the present invention is a kit comprising an effective dose of (i) a quinonemethide triterpenoid as described above;
(ii) at least one chemotherapeutic compound selected from the group consisting of a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog. Said chemotherapeutic compound is in particular selected from cisplatin, doxorubicin, taxol, etoposide and staurosporine or mixtures thereof, more preferably from doxorubicin or taxol, most preferably from taxol.

The kit may further comprise an instruction leaflet and/or means for determining ABC-protein, in particular P-glycoprotein, expression or functional activity or pro-apoptotic protein, such as p53, Bax or Bak, expression or pro-apoptotic activity. The kit may comprise excipients, in particular pharmaceutically acceptable excipients, such as a carrier, salt, buffer, water, or a combination thereof. The skilled person is able to select suitable excipients. Still further, the kit may comprise at least one container.

The quinonemethide triterpenoid according to the invention can be present in solid, semisolid or liquid form to be administered by an oral, rectal, topical, parenteral or transdermal or inhalative route to a subject, preferably a human.

Preferably, the quinonemethide triterpenoid in the kit has a structure of Formula (IIIa) or (IIIb):

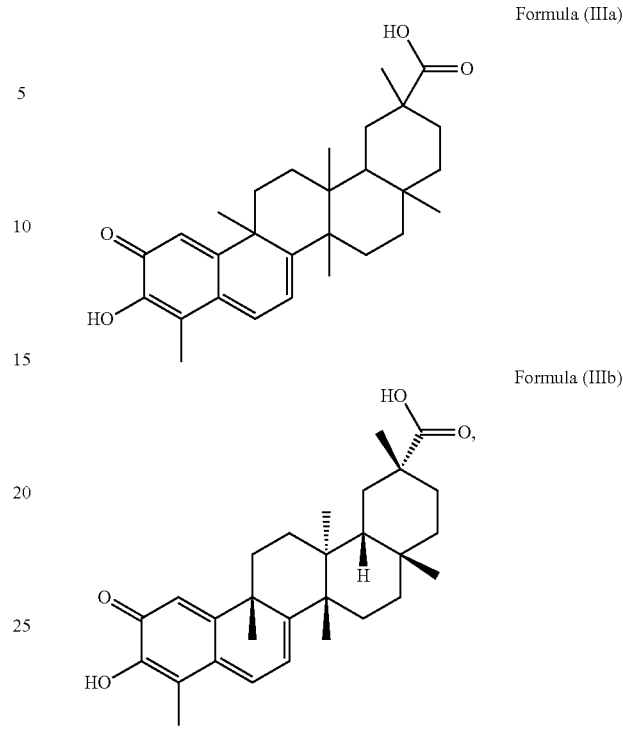

Formula (IIIa)

Formula (IIIb)

and the chemotherapeutic compound is taxol or doxorubicin, most preferably the chemotherapeutic compound is taxol Still another aspect of the present invention concerns the use of the quinonemethide triterpenoid of the present invention or the kit described above for inhibiting P-glycoprotein in multidrug-resistant cancer and cancer cells, respectively, in particular for initiating cell death of multidrug-resistant cancer cells or for inducing collateral sensitivity in said multidrug-resistant cancer cells.

The inhibition of P-glycoprotein can be determined with a P-glycoprotein efflux assay by determining the amount of multidrug-resistant cancer cells in a sample with marker such as with Rho123 in the presence of the quinonemethide triterpenoid of the present invention after carrying out the efflux assay compared to a reference control with multidrug-resistant cancer cells in the absence of the quinonemethide triterpenoid. In particular, the percentage of cells with marker such as Rho123 is at least 15, further preferably at least 20, more preferably at least 30 and in particular at least 40 percentage points and more preferably more than 50 percentage points increased compared to the reference control by the quinonemethide triterpenoid of the present invention. Usually, the multidrug-resistant cancer cells are contacted with the quinonemethide triterpenoid and incubated for at least 12 h, in particular for about 24 h at about 37° C. The reference control is, instead, not incubated with the quinonemethide triterpenoid. Usually, the marker in particular Rho123 is subsequently added while further incubating at about 37° C. for at least 20 min, preferably for at least 30 min and in particular for about 1 h.

EXAMPLES

Example 1

Molecular Docking Studies

The previously generated homology model of human P-glycoprotein (further referenced as "P-gp") was used for molecular docking studies with AutoDock 4 on the drug binding pocket. The residues at the drug binding pocket are: His61, Gly64, Leu65, Met69, Ser222, Leu304, Ile306, Tyr307, Phe336, Leu339, Ile340, Ala342, Phe343, Gln725, Phe728, Phe732, Leu762, Thr837, Ile868, Gly872, Phe942, Thr945, Tyr953, Leu975, Phe978, Ser979, Val982, Gly984, Ala985, Met986, Gly989, Gln990, and Ser993 (Aller, S. G. et al., Science 2009, 323:1718-22). A grid map was chosen to cover these residues. Two independent docking calculations for celastrol and verapamil were conducted with 2,500,000 evaluations and 250 runs using Lamarckian Genetic Algorithm. The lowest binding energies (LBE) and predicted inhibition constants were obtained from the docking log files (dlg) and mean±SD values were calculated. For visualization of the docking results, Visual Molecular Dynamics (VMD) was used. VMD software was developed with NIH support by the Theoretical and Computational Biophysics group at the Beckman Institute, University of Illinois at Urbana-Champaign. For co-docking calculations, verapamil and celastrol were selected to evaluate the effect of pre-docked compound on binding energies and docking pose.

Celastrol showed different docking pose (R-site) and higher LBE value (−11.94±0.00 kcal/mol) compared to verapamil (−11.26±0.59 kcal/mol) on the M-site of drug binding pocket of P-gp (FIG. 1). This demonstrated that celastrol strongly bonded and inhibited P-gp protein by forming two hydrogen bonds with amino acids Lys 290 and Lys 826, whereas verapamil only formed hydrogen bonds with amino acid Tyr 953 within its drug binding pocket. These findings suggest that celastrol is a suitable and potent P-gp inhibitor compared to verapamil.

Example 2

Inhibition of P-gp Efflux Pump Activity in A549 Taxol-Resistant Lung Cancer Cells A Rho123 efflux assay has been carried out in order to determine the P-gp functional activity and the inhibitory effects of the compound of Formula (IIIb) on P-gp. A549 taxol-resistant lung cancer cells were seeded in 6 well-plates at a final concentration of $2 \times 10^5$ cells per well and cultured for 24 h at 37° C. in an atmosphere containing 5% $CO_2$. At confluence, 3 mL fresh media with or without 0.1, 0.2, 0.5 and 1 µM celastrol, or 10 µM verapamil (known P-gp inhibitor) was added and further incubated at 3° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 µL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

As shown in FIG. 2A to 2G, Rho123 dye staining in taxol-resistant lung cancer cells only yielded 20% of cell population with fluorescence signal, suggesting that P-gp in these taxol-resistant cancer cells effectively pumped out the Rho123 dye from the cells. However, addition of the P-gp inhibitor verapamil significantly suppressed the P-gp activity, leading to markedly increase of Rho123 fluorescence signal in cells. Meanwhile, celastrol at relative low concentrations inhibited the P-gp activity dose-dependently, thereby increased the Rho123 accumulation in taxol-resistant cancer cells. Collectively, these results again confirm that celastrol is a potent P-gp inhibitor compared to verapamil.

Example 3

Combination of Compound of Formula (IIIb) with Taxol in A549 Taxol-Resistant Lung Cancer Cells Cell cultures and cytotoxicity assays have been carried out. Celastrol was dissolved in DMSO at a final concentration of 100 mmol/L and stored at −20° C. Cytotoxicity was assessed using the 3-(4,5-dimethylthiazol-2-yl)-2,5-diphenyltetrazolium bromide assay. 4000 cells from A549 taxol-resistant lung cancer cells were seeded on 96-well plates per well. After overnight pre-incubation, the cells were exposed to different concentrations of taxol (0.019-100 µmol/L) in the presence or absence of celastrol (0.5 µM) for 3 days. Subsequently, 10 µL of MTT reagents was added to each well and incubated at 37° C. for 4 hours followed by the addition of 100 µL solubilization buffer (10% SDS in 0.01 mol/L HCl) and overnight incubation. Absorbance at 585 nm was determined from each well the next day. The percentage of cell viability was calculated using the following formula: Cell viability (%)=Cells number treated/Cells number DMSO control×100. Data were obtained from three independent experiments.

Annexin V flow cytometry analysis has been carried out. Cell death and viability were measured using an Annexin V staining kit (BD Biosciences, San Jose, Calif., USA).

Briefly, A549 taxol-resistant cancer cells were treated with 0.1-0.5 µM celastrol with or without 40 µM of taxol for 24 h. Cells were then harvested and analysed by multiparametric flow cytometry using FITC-Annexin V and propidium iodide staining (BD Biosciences, San Jose, Calif., USA) according to the manufacturer's instructions. Flow cytometry was then carried out using a FACSCalibur flow cytometer (BD Biosciences, San Jose, Calif., USA). Data acquisition and analysis was performed with CellQuest (BD Biosciences, San Jose, Calif., USA). Data were obtained from three independent experiments.

Figure 3:
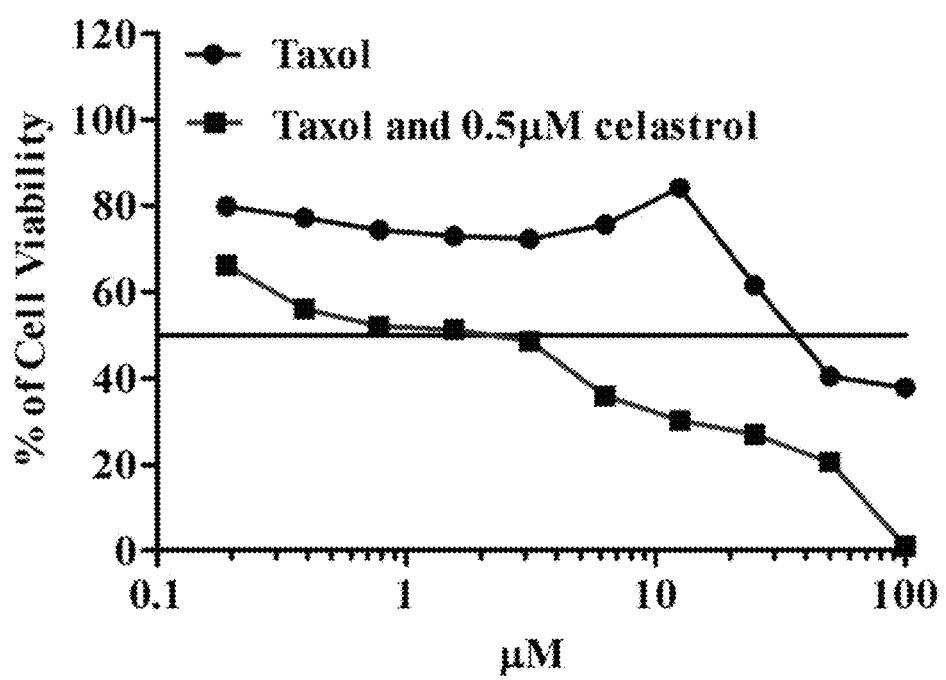
FIG. 3 is a cell cytotoxicity graph comparing A549 taxol-resistant lung cancer cells treated with taxol in the presence or absence of celastrol.
Figure 4A:
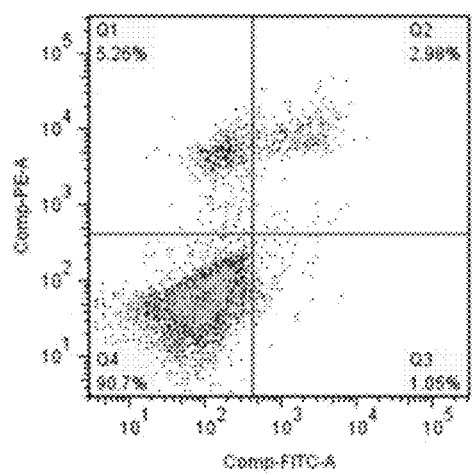
FIG. 4A to 4H refer to an Annexin V flow cytometry analysis of cell death in A549 taxol-resistant lung cancer cells. These cancer cells were treated with 0.1, 0.2 and 0.5 µM of celastrol in the presence or absence of taxol (40 µM) and compared to a control group.
Figure 4B:
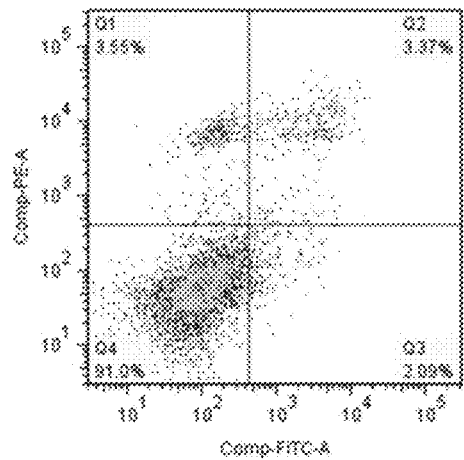
Figure 4C:
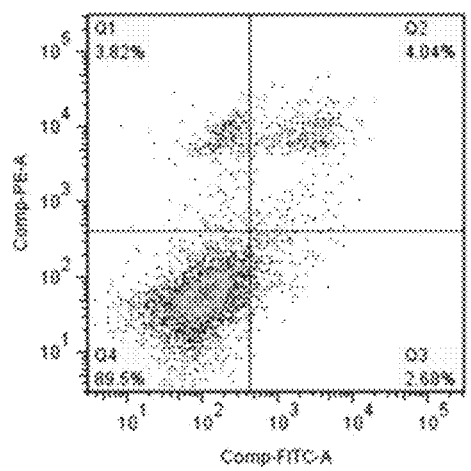
Figure 4D:
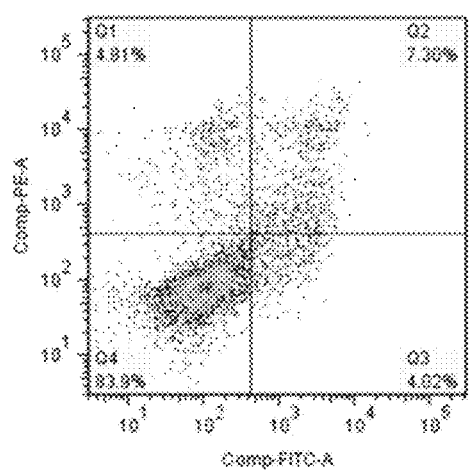
Figure 4E:
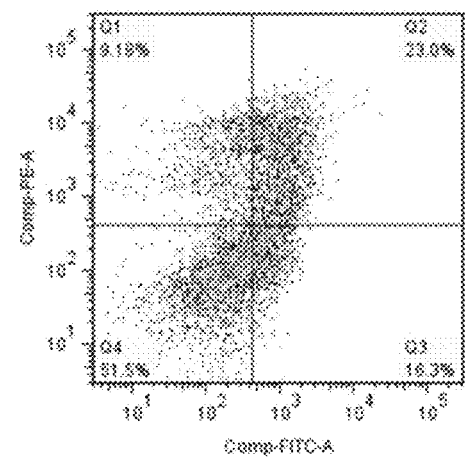
Figure 4F:
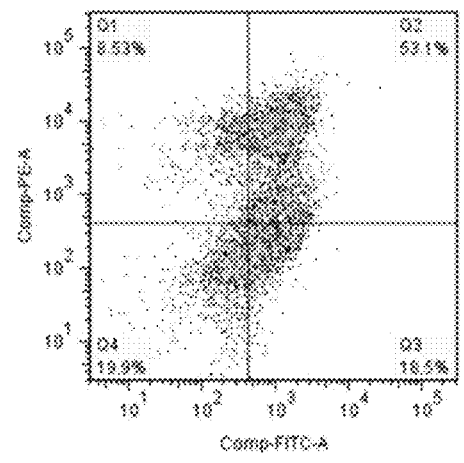
Figure 4G:
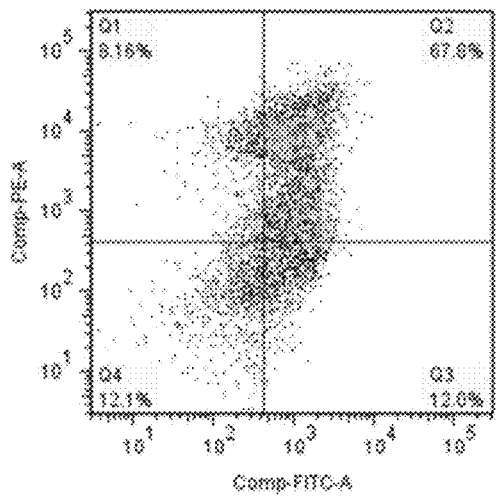
Figure 4H:
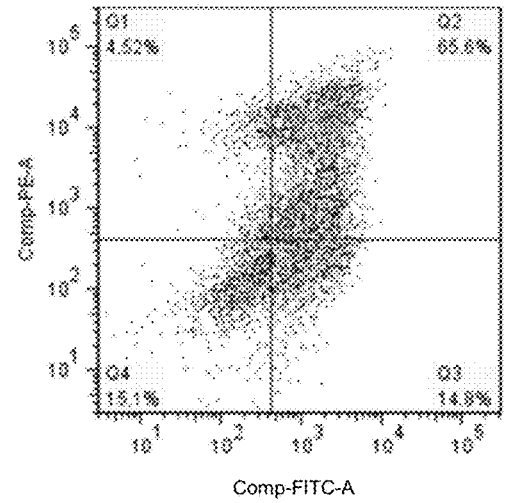
Figure 4I:
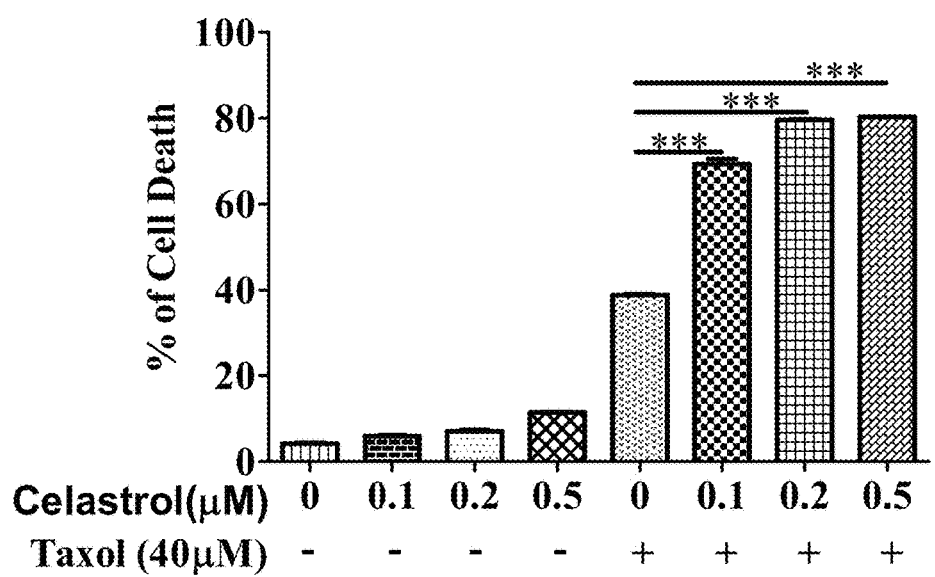
FIG. 4I is a bar chart showing the percentages of cell death in A549 taxol-resistant lung cancer cells in the presence or absence of taxol compared to a control group.

As shown in FIG. 3, MTT cytotoxicity assay showed that the mean $IC_{50}$ of taxol in A549 taxol-resistant cancer cells was 36 µM. However, when the cells were co-treated with taxol in the presence of 0.5 µM celastrol, the mean $IC_{50}$ of taxol in A549 taxol-resistant cancer cells was markedly reduced to 2.17 µM. In addition, to further address whether the inhibition of P-gp by celastrol could potentiate and sensitize the taxol-resistant cancer cells towards chemotherapeutic compounds, the A549 taxol-resistant lung cancer cells were treated with celastrol with or without taxol. As shown in FIG. 4A to 4H, A549 taxol-resistant lung cancer cells treated with 0.1-0.5 µM of celastrol demonstrated limited cytotoxicity, whereas in the cancer cells co-treated with celastrol the taxol-mediated cytotoxicity in these drug-resistant cancers was significantly enhanced. Collectively, these findings further support that celastrol is a potent P-gp inhibitor to reverse the drug-resistant phenotype of taxol-resistant cancer cells.

Example 4

Cytotoxic Effect Toward ABCB5 and Breast Cancer Resistant Protein (BCRP) Overexpressing Cancer Cells Cell cultures and cytotoxicity assays have been used. Celastrol was dissolved in DMSO at a final concentration of 100 mmol/L and stored at −20° C. Cytotoxicity was assessed using the 3-(4,5-dimethylthiazol-2-yl)-2,5-diphenyltetrazolium bromide assay. 4000 cells from HEK293 and HEK293/ABCB5 kidney cancer cells or MDA-MB-231 pcDNA and MDA-MB-231/BCRP breast cancer cells were seeded on 96-well plates per well. After overnight pre-incubation, the cells were exposed to different concentrations of celastrol (0.1-10 μmol/L) for 3 days. Subsequently, 10 μL of MTT reagents were added to each well and incubated at 37° C. for 4 hours followed by the addition of 100 μL solubilization buffer (10% SDS in 0.01 mol/L HCl) and overnight incubation. Absorbance at 585 nm was determined from each well the next day. The percentage of cell viability was calculated using the following formula: Cell viability (%)=Cells number treated/Cells number DMSO control×100. Data were obtained from three independent experiments.

Figure 5A:
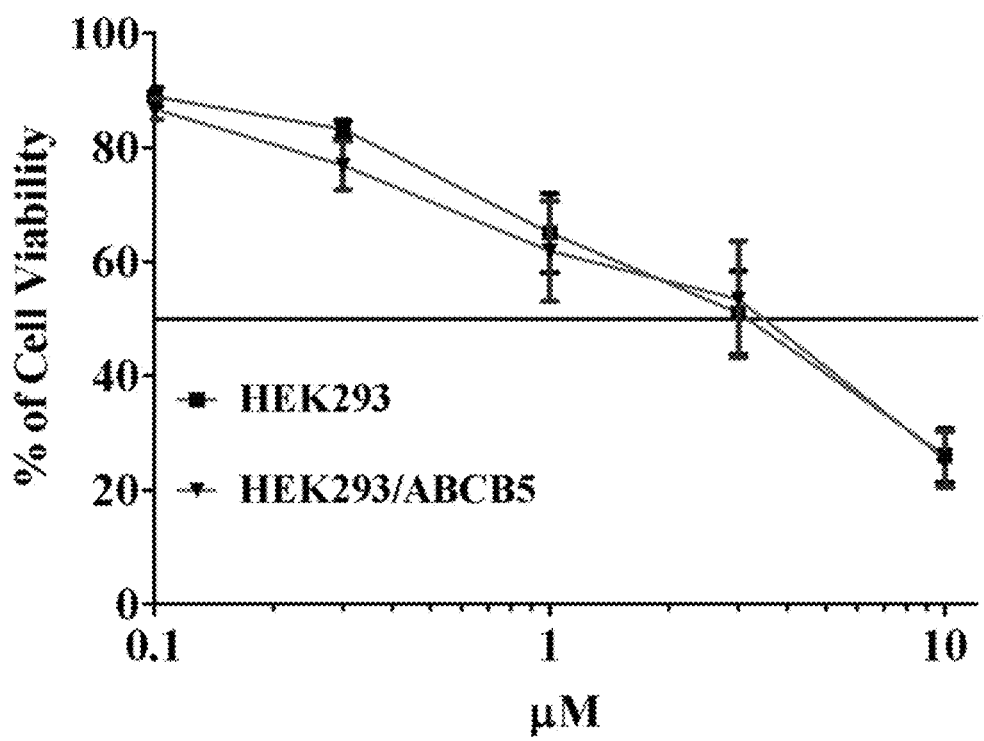
FIG. 5A is a graph showing the cytotoxic effect of celastrol on wild-type or ABCB5 overexpressing HEK293 kidney cells.

Given that P-gp is the direct target of celastrol, it has been further investigated whether celastrol is the substrate of ABCB5 and overexpression of such protein would abolish the cytotoxic effect of celastrol. The cytotoxicity of celastrol in HEK293 wild-type and ABCB5 overexpressing kidney cells has therefore been analyzed. As shown in FIG. 5A and table 1, celastrol demonstrated similar cytotoxic potency in ABCB5 overexpressing kidney cancer cells with resistant factor 1.12.

TABLE 1

$IC_{50}$ of celastrol on wild-type or ABCB5 overexpressing HEK293 kidney cells

| Compound | HEK293 (Kidney) | HEK293/ABCB5 (Kidney) | Resistant Factor |
|---|---|---|---|
| Celastrol | 3.08 μM | 3.45 μM | 1.12 |

Figure 5B:
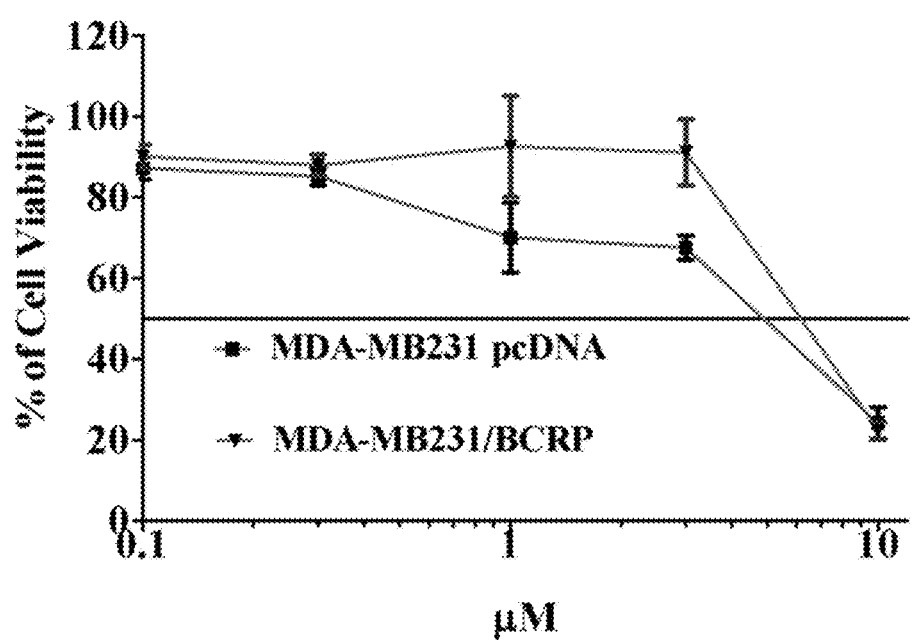
FIG. 5B is a graph to show the cytotoxic effect of celastrol on wild-type or breast cancer resistant protein (BCRP) overexpressing MDA-MB-231 breast cancer cells.
Figure 6A:
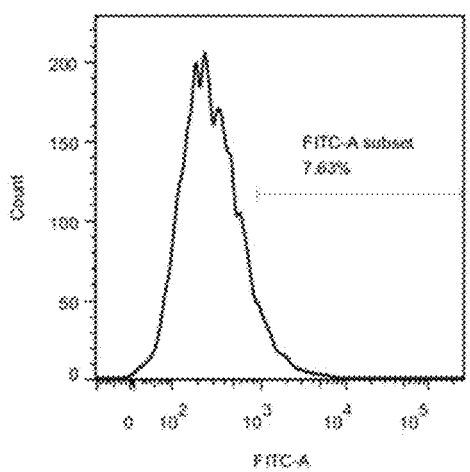
FIG. 6A to FIG. 6E show curves obtained with flow cytometry analysis of a Rho123 efflux assay in A549 taxol-resistant lung cancer cells. These cancer cells were treated with Rho123 dye in the presence of the P-glycoprotein inhibitor verapamil (10 µM) or 0.5 µM celastrol (compound of Formula (IIIb), 0.5 µM pristimerin (compound of Formula (IV) or 0.5 µM dihydrocelastrol (compound of Formula (VI) and compared with a Rho123 control group.
Figure 6B:
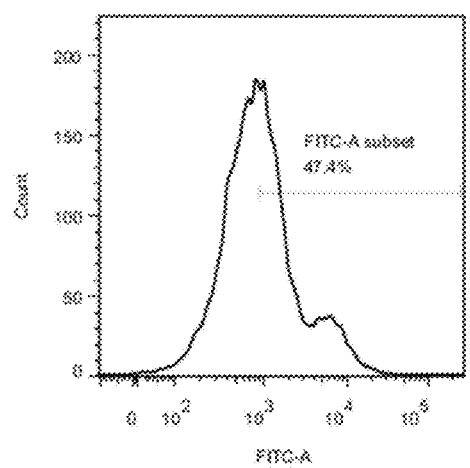
Figure 6C:
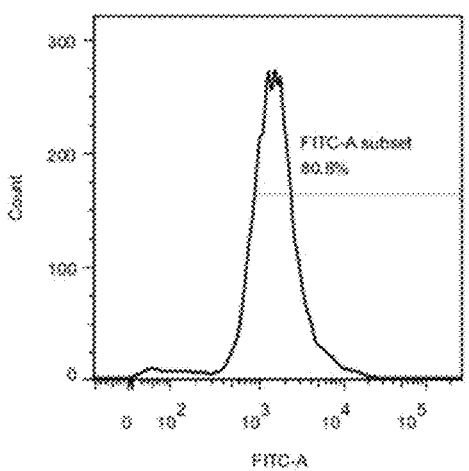
Figure 6D:
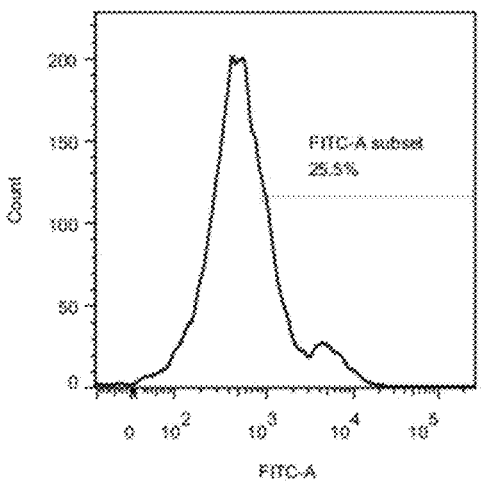
Figure 6E:
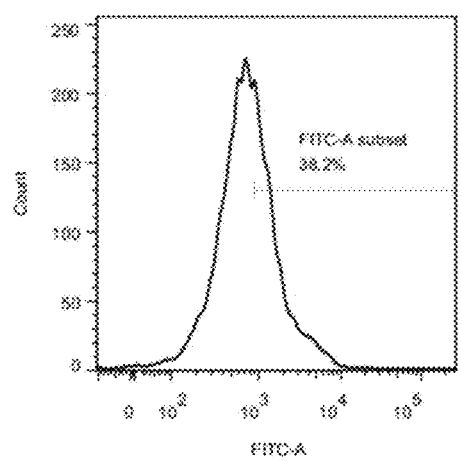
Figure 6F:
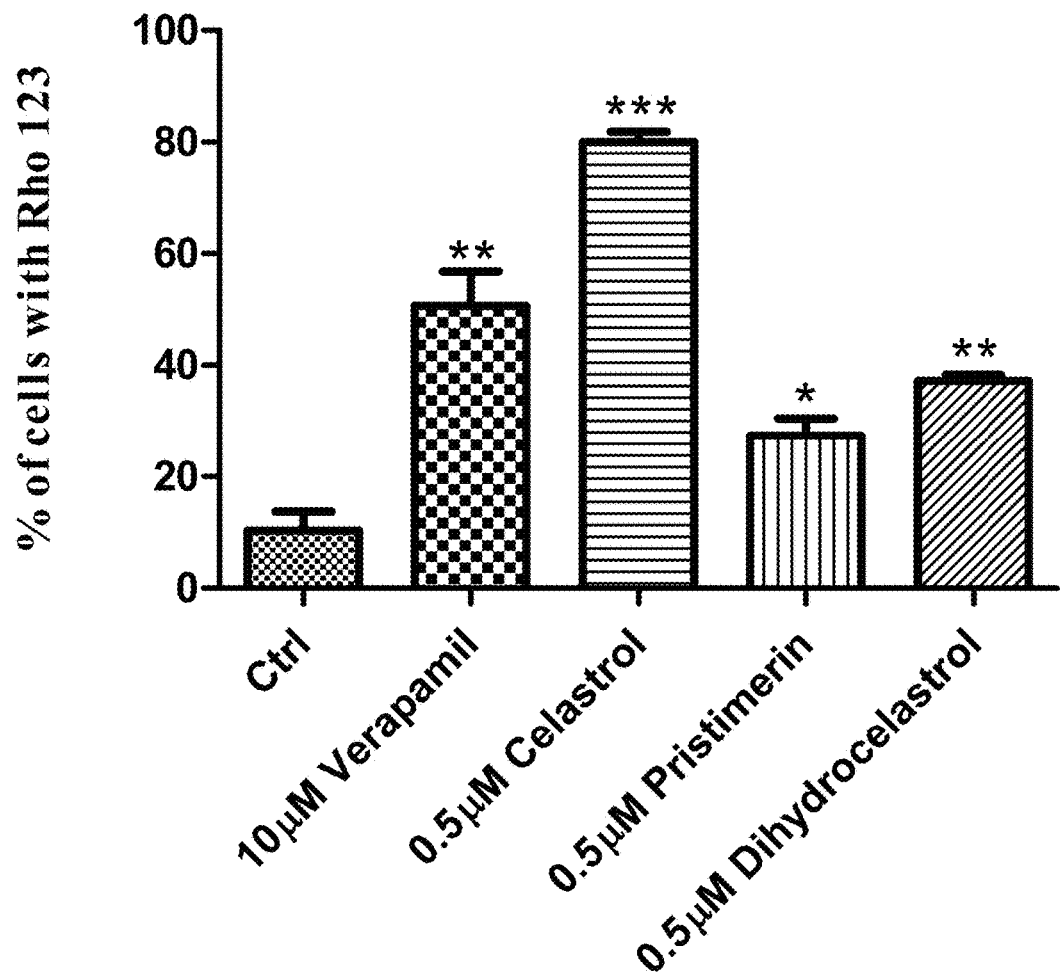
FIG. 6F is a bar chart showing the percentage of cells with Rho123 in verapamil-treated A549 taxol-resistant lung cancer cells or A549 taxol-resistant lung cancer cells treated with a quinonemethide triperpenoid of the present invention compared to a Rho123 control group.

In addition, the effect of celastrol in breast cancer resistant protein (BCRP) overexpressing cancer cells has been analyzed. As shown in FIG. 5B and table 2, celastrol also showed similar cytotoxicity toward the BCRP overexpressing breast cancer cells with resistant factor 1.28. These findings suggest that celastrol is not the substrate of drug-resistant proteins P-gp or BCRP, overexpression of these proteins would not abolish the cytotoxic potency of celastrol toward these resistant cancer cells.

TABLE 2

$IC_{50}$ of celastrol on wild-type or breast cancer resistant protein (BCRP) overexpressing MDA-MB-231 breast cancer cells

| Compound | MDA-MB-231 pcDNA (Breast) | MDA-MB-231/ BCRP (Breast) | Resistant Factor |
|---|---|---|---|
| Celastrol | 4.83 μM | 6.19 μM | 1.28 |

Example 5

Cytotoxic Potency of the Compound of Formula (IIIb) in Apoptosis-Deficient Multidrug-Resistant Cancers Cell cultures and cytotoxicity assays have been used. Celastrol was dissolved in DMSO at a final concentration of 100 mmol/L and stored at −20° C. Cytotoxicity was assessed using the 3-(4,5-dimethylthiazol-2-yl)-2,5-diphenyltetrazolium bromide assay. 4000 cells from HCT116 $p53^{+/+}$ or $p53^{-/-}$ colon cancer cells and DLD-1 Bax-Bak$^{+/+}$ or Bax-Bak$^{-/-}$ colon cancer cells were seeded on 96-well plates per well. After overnight pre-incubation, the cells were exposed to different concentrations of celastrol (0.039-100 μmol/L) or other chemotherapeutic compounds such as cisplatin, doxorubicin, taxol, etoposide and staurosporine for 3 days. Subsequently, 10 μL of MTT reagents were added to each well and incubated at 37° C. for 4 hours followed by the addition of 100 μL solubilization buffer (10% SDS in 0.01 mol/L HCl) and overnight incubation. Absorbance at 585 nm was determined from each well the next day. The percentage of cell viability was calculated using the following formula: Cell viability (%)=Cells number treated/Cells number DMSO control×100. Data were obtained from three independent experiments.

Collateral sensitivity is a phenomenon, where multidrug-resistant cells are hypersensitive to a compound compared to otherwise drug-sensitive cells. Hence, collateral sensitivity provides a unique opportunity to specifically kill multidrug-resistant cancer cells. Given that the tumor suppressor p53 is a sensor of cellular stress and also a critical mediator of apoptosis, extensive studies showed that the high frequency of p53 mutations can lead to drug resistance of cancer cells. Therefore, the cytotoxic potency of celastrol has been evaluated using the isogenic HCT116 p53 wild-type and deficient colon cancer cells. As shown in table 3, the HCT116 p53 wild-type and deficient colon cancer cells demonstrated a significant drug-resistant phenotype toward a panel of chemotherapeutic compounds including cisplatin, doxorubicin, taxol, etoposide and staurosporine with resistant factors from 11.28 to 92.37. In contrast, celastrol showed much better cytotoxic potency in HCT116-p53 deficient colon cancer cells with resistant factor 0.58 only (table 3).

TABLE 3

$IC_{50}$ and resistant factor of isogenic p53 wild-type versus p53-deficient HCT116 colon cancer cells toward the treatment of cisplatin, doxorubicin, taxol, etoposide, staurosporine and celastrol

| Compound | HCT116 $p53^{+/+}$ colon cancer cells | HCT116 $p53^{-/-}$ colon cancer cells | Resistant Factor |
|---|---|---|---|
| Cisplatin | 0.19 μM | 17.55 μM | 92.37 |
| Doxorubicin | 0.52 μM | 10.15 μM | 19.52 |
| Taxol | 19.5 nM | 251 nM | 12.87 |
| Etoposide | 0.94 μM | 10.6 μM | 11.28 |
| Staurosporine | 3.69 nM | 48 nM | 13.01 |
| Celastrol | 0.831 μM | 0.484 μM | 0.58 |

Concomitantly, similar findings were obtained in other isogenic cancer cells with double knockout of apoptotic genes, Bax and Bak. Studies showed that tumor cells lacking essential cell death mediators Bax and Bak, namely lacking these pro-apoptotic proteins, will also develop resistance to elude various apoptosis-stimuli. The cytotoxic effect of celastrol has been determined in the isogenic DLD-1 Bax- Bak wild-type and deficient colon cancer cells. As shown in table 4, the DLD-1 Bax-Bak wild-type and Bax-Bak deficient colon cancer cells also presented a significant drug-resistant phenotype toward the above tested chemotherapeutic compounds with resistant factors ranging from 1.84 to >23.2. Consistently, celastrol also indicated much better cytotoxic potency in DLD-1 Bax-Bak$^{-/-}$ colon cancer cells with resistant factor 0.32 only (table 4). Collectively, these results confirm that celastrol exhibits collateral sensitivity toward these apoptosis-deficient multidrug-resistant cancer cells.

TABLE 4

$IC_{50}$ and resistant factor of isogenic Bax-Bak wild-type versus Bax-Bak deficient DLD-1 colon cancer cells toward the treatment of cisplatin, doxorubicin, taxol, etoposide, staurosporine and celastrol

| Compound | DLD-1 Bax-Bak$^{+/+}$ colon cancer cells | DLD-1 Bax-Bak$^{-/-}$ colon cancer cells | Resistant Factor |
|---|---|---|---|
| Cisplatin | 1994 ng/mL | 3678 ng/mL | 1.84 |
| Doxorubicin | 52.3 ng/mL | 539 ng/mL | 10.31 |
| Taxol | 4.31 mM | >100 mM | >23.2 |
| Etoposide | 2.36 μM | 40.4 μM | 17.12 |
| Staurosporine | 29.1 nM | >100 nM | 3.34 |
| Celastrol | 0.575 μM | 0.184 μM | 0.32 |

Example 6

Cytotoxic Potency of the Compound of Formula (IIIb) in Taxol-Resistant Cancer Cells from Different Human Origins Cell cultures and cytotoxicity assays have been used. Celastrol was dissolved in DMSO at a final concentration of 100 mmol/L and stored at −20° C. Cytotoxicity was assessed using the 3-(4,5-dimethylthiazol-2-yl)-2,5-diphenyltetrazolium bromide assay. 4000 cells from A549 (lung), A2780 (ovary), HCT-8 (colon) and MCF-7 (breast) cancer cells were seeded on 96-well plates per well. After overnight pre-incubation, the cells were exposed to different concentrations of celastrol (0.039-100 μmol/L) or taxol for 3 days. Subsequently, 10 μL of MTT reagents was added to each well and incubated at 37° C. for 4 hours followed by the addition of 100 μL solubilization buffer (10% SDS in 0.01 mol/L HCl) and overnight incubation. Absorbance at 585 nm was determined from each well the next day. The percentage of cell viability was calculated using the following formula: Cell viability (%)=Cells number treated/Cells number DMSO control×100. Data were obtained from three independent experiments.

A549 taxol-sensitive/-resistant cancer cells demonstrated a significant drug-resistant phenotype in response to taxol treatment with over 894 resistant factor, whereas celastrol showed more cytotoxic effect toward the taxol-resistant lung cancer cells with resistant factor 0.42 (table 5). Beside, A2780 taxol-sensitive/-resistant ovarian cancer cells demonstrated a marked resistance toward the taxol treatment with resistant factor over 62000, whereas celastrol even showed more cytotoxic potency in taxol-resistant ovarian cancer cells (resistant factor: 0.6) (table 6). In other taxol-resistant cancer cells, taxol exhibited 5000 to 31000 resistant factor in MCF-7 (breast) and HCT-8 (colon) taxol-resistant cancer cells respectively compared with their taxol-sensitive parental cells (table 7 and table 8). In contrast, celastrol showed much better cytotoxic potency in both MCF-7 and HCT-8 taxol-resistant cancer cells with resistant factor from 0.59 to 0.65 only (table 5 and table 6). Collectively, these results further confirm that celastrol exhibits collateral sensitivity toward the taxol-resistant cancer cells from different human origins.

TABLE 5

$IC_{50}$ and resistant factor of taxol-sensitive versus taxol-resistant A549 lung cancer cells toward the treatment of taxol and celastrol

| Compound | A549 (Lung) (Taxol sensitive) | A549 (Lung) (Taxol resistant) | Resistant Factor |
|---|---|---|---|
| Taxol | 34 nM | 30.4 μM | 894.12 |
| Celastrol | 2.4 μM | 1.0 μM | 0.42 |

TABLE 6

$IC_{50}$ and resistant factor of taxol-sensitive versus taxol-resistant A2780 ovarian cancer cells toward the treatment of taxol and celastrol

| Compound | A2780 (Ovary) (Taxol sensitive) | A2780 (Ovary) (Taxol resistant) | Resistant Factor |
|---|---|---|---|
| Taxol | <1 nM | 62 μM | >62000 |
| Celastrol | 0.902 μM | 0.54 μM | 0.60 |

TABLE 7

$IC_{50}$ and resistant factor of taxol-sensitive versus taxol-resistant HCT-8 colon cancer cells toward the treatment of taxol and celastrol

| Compound | HCT-8 (Colon) (Taxol sensitive) | HCT-8 (Colon) (Taxol resistant) | Resistant Factor |
|---|---|---|---|
| Taxol | <1 nM | 32 μM | >31000 |
| Celastrol | 0.937 μM | 0.553 μM | 0.59 |

TABLE 8

$IC_{50}$ and resistant factor of taxol-sensitive versus taxol-resistant MCF-7 breast cancer cells toward the treatment of taxol and celastrol

| Compound | MCF-7 (Breast) (Taxol sensitive) | MCF-7 (Breast) (Taxol resistant) | Resistant Factor |
|---|---|---|---|
| Taxol | <1 nM | 5 μM | 5000 |
| Celastrol | 1.12 μM | 0.730 μM | 0.65 |

Example 7

Cytotoxic Potency of the Compound of Formula (IIIb) in Doxorubicin-Resistant Cancer Cells from Different Human Origins Cell cultures and cytotoxicity assays have been used. Celastrol was dissolved in DMSO at a final concentration of 100 mmol/L and stored at −20° C. Cytotoxicity was assessed using the 3-(4,5-dimethylthiazol-2-yl)-2,5-diphenyltetrazolium bromide assay. 4000 cells from MCF-7 doxorubicin sensitive/resistant breast cancer cells or CEM doxorubicin sensitive/resistant leukemia cells were seeded on 96-well plates per well. After overnight pre-incubation, the cells were exposed to different concentrations of celastrol (0.039-100 μmol/L) or doxorubicin for 3 days. Subsequently, 10 μL of MTT reagents were added to each well and incubated at 37° C. for 4 hours followed by the addition of 100 μL solubilization buffer (10% SDS in 0.01 mol/L HCl) and overnight incubation. Absorbance at 585 nm was determined from each well the next day. The percentage of cell viability was calculated using the following formula: Cell viability (%)=Cells number treated/Cells number DMSO control× 100. Data were obtained from three independent experiments.

MCF-7 doxorubicin-sensitive/-resistant breast cancer cells demonstrated a significant drug-resistant phenotype in response to doxorubicin treatment with 21.6 resistant factor, whereas celastrol showed more cytotoxicity toward the doxorubicin-resistant breast cancer cells with resistant factor 0.84 (table 9). Beside, CEM doxorubicin-sensitive/-resistant leukemia cells demonstrated a marked resistance toward the doxorubicin treatment with resistant factor over 5000, whereas celastrol even showed extreme cytotoxic potency in doxorubicin-resistant leukemia cells (resistant factor: 0.033) (table 10). Collectively, these results strongly suggest that celastrol exhibits collateral sensitivity toward the doxorubicin-resistant cancer cells from different human origins.

TABLE 9

$IC_{50}$ and resistant factor of doxorubicin-sensitive versus doxorubicin-resistant MCF-7 breast cancer cells toward the treatment of doxorubicin and celastrol

| Compound | MCF-7 (Breast) (Doxorubicin sensitive) | MCF-7 (Breast) (Doxorubicin resistant) | Resistant Factor |
|---|---|---|---|
| Doxorubicin | 463 ng/mL | 10000 ng/mL | 21.6 |
| Celastrol | 1.13 µM | 0.950 µM | 0.84 |

TABLE 10

$IC_{50}$ and resistant factor of doxorubicin-sensitive versus doxorubicin-resistant CEM leukemia cells toward the treatment of doxorubicin and celastrol

| Compound | CCRF-CEM (Leukemia) (Doxorubicin sensitive) | CEM-ADR5000 (Leukemia) (Doxorubicin resistant) | Resistant Factor |
|---|---|---|---|
| Doxorubicin | * | * | >1000 |
| Celastrol | 3.26 µM | 0.108 µM | 0.033 |

* Efferth, T. et al., Clinical Cancer Research, 2008, 14: 2405-2412.

Example 8

Cytotoxic Potency of the Compound of Formula (IIIb) in Cisplatin-Resistant Cancer Cells from Different Human Origins Cell cultures and cytotoxicity assays have been used. Celastrol was dissolved in DMSO at a final concentration of 100 mmol/L and stored at −20° C. Cytotoxicity was assessed using the 3-(4,5-dimethylthiazol-2-yl)-2,5-diphenyltetrazolium bromide assay. 4000 cells from A2780 cisplatin sensitive/resistant ovarian cancer cells or SGC-7901 cisplatin sensitive/resistant gastric cancer cells were seeded on 96-well plates per well. After overnight pre-incubation, the cells were exposed to different concentrations of celastrol (0.039-100 µmol/L) or cisplatin for 3 days. Subsequently, 10 µL of MTT reagents were added to each well and incubated at 37° C. for 4 hours followed by the addition of 100 µL solubilization buffer (10% SDS in 0.01 mol/L HCl) and overnight incubation. Absorbance at 585 nm was determined from each well the next day. The percentage of cell viability was calculated using the following formula: Cell viability (%)=Cells number treated/Cells number DMSO control× 100. Data were obtained from three independent experiments.

A2780 cisplatin-sensitive/-resistant ovarian cancer cells demonstrated a significant drug-resistant phenotype in response to cisplatin treatment with 14.92 resistant factor, whereas celastrol showed similar cytotoxicity toward both cisplatin sensitive/resistant ovarian cancer cells with resistant factor 1.03 (table 11). Beside, SGC-7901 cisplatin-sensitive/-resistant gastric cancer cells demonstrated a marked resistant toward the cisplatin treatment with resistant factor 4.9, whereas celastrol even showed better cytotoxic potency in cisplatin-resistant gastric cancer cells (resistant factor: 0.88) (table 12). Collectively, these results further confirm that celastrol exhibits potent cytotoxicity toward the cisplatin-resistant cancer cells from different human origins.

TABLE 11

$IC_{50}$ and resistant factor of cisplatin-sensitive versus cisplatin-resistant A2780 ovarian cancer cells toward the treatment of cisplatin and celastrol

| Compound | A2780 (Ovary) (Cisplatin sensitive) | A2780 (Ovary) (Cisplatin resistant) | Resistant Factor |
|---|---|---|---|
| Cisplatin | 1.24 µM | 18.5 µM | 14.92 |
| Celastrol | 0.525 µM | 0.543 µM | 1.03 |

TABLE 12

$IC_{50}$ and resistant factor of cisplatin-sensitive versus cisplatin-resistant SGC-7901 gastric cancer cells toward the treatment of cisplatin and celastrol

| Compound | SGC-7901 (Gastric) (Cisplatin sensitive) | SGC-7901 (Gastric) (Cisplatin resistant) | Resistant Factor |
|---|---|---|---|
| Cisplatin | 1.26 µM | 6.19 µM | 4.9 |
| Celastrol | 1.94 µM | 1.72 µM | 0.88 |

Example 9

Comparison of Further Quinonemethide Triterpenoids of the Present Invention and their P-gp Efflux Pump Activity in A549 Taxol-Resistant Lung Cancer Cells A Rho123 efflux assay has been carried out in order to compare the P-gp functional activity and the inhibitory effects of other quinonemethide triterpenoids of the present invention on P-gp. A549 taxol-resistant lung cancer cells were seeded in 6 well-plates at a final concentration of $2\times10^5$ cells per well and cultured for 24 h at 37° C. in an atmosphere containing 5% $CO_2$. At confluence, 3 mL fresh media with or without 0.5 µM celastrol, 10 µM verapamil (known P-gp inhibitor), 0.5 µM pristimerin (compound of Formula (IV) and 0.5 µM dihydrocelastrol (compound of Formula (VI) was added and further incubated at 3° C. for 24 h. Subsequently, 5 mg/mL Rho123 was added to each well and the wells were incubated for another 1 h at 37° C. At the end of the incubation, the accumulation of Rho123 was stopped by washing the cells five times with ice-cold PBS. After cell centrifugation, cell pellets were resuspended in 400 µL PBS. Intracellular fluorescence was measured using a flow cytometer at an excitation wavelength of 488 nm and emission wavelength of 525 nm. All data acquisition and analyses were performed with CellQuest (BD Biosciences, San Jose, Calif., USA) in triplicate in three independent experiments, and the results were shown as the mean of fluorescence intensity.

As shown in FIG. 6A to FIG. 6F, Rho123 dye staining in taxol-resistant lung cancer cells only yielded ~12% of cell population with fluorescence signal, suggesting that P-gp in these taxol-resistant cancer cells effectively pumped out the Rho123 dye from the cells. However, addition of the P-gp inhibitor verapamil significantly suppressed the P-gp activity, leading to markedly increased Rho123 fluorescence signal in cells. Meanwhile, celastrol at relative low concentrations inhibited the P-gp activity dose-dependently, thereby increased the Rho123 accumulation in taxol-resistant cancer cells. Other quinonemethide triterpenoids of the present invention such as pristimerin and dihydrocelastrol showed P-pg inhibition, but with a different extent and were in the concentration tested less potent compared to celastrol. Collectively, these results further confirm that quinonemethide triterpenoids of the present invention, namely of Formula (I), are potent P-gp inhibitors compared to verapamil.

The invention claimed is:

1. A method for treating a subject suffering from a multidrug-resistant apoptosis-deficient cancer with decreased pro-apoptotic protein activity comprising the step of administering an effective amount of a quinonemethide triterpenoid or a pharmaceutically tolerable salt, solvate or anhydrate thereof to a human subject, wherein the quinonemethide triterpenoid has a structure of

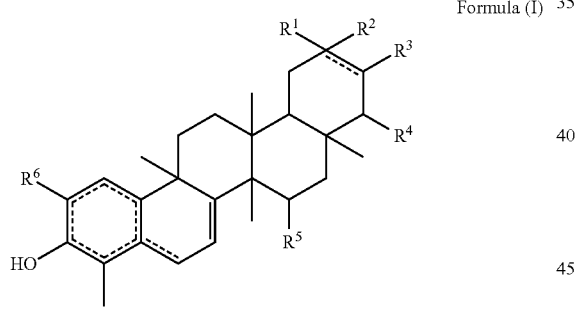

Formula (I), wherein - - represents a single or double bond; —R1 is selected from —CH3, —CH2OH, —OH or —H; —R2 is selected from —CH3, —CH2OH, —OH, —COOH, =CH2 or —H; —R3 is selected from —OH, =O or —H; —R4 is selected from —OH or —H; —R5 is selected from —OH or —H; and —R6 is selected from =O or —OH; wherein the multidrug-resistant apoptosis-deficient cancer is selected from at least one of a multidrug-resistant p53-deficient, multidrug-resistant Bax-deficient or multidrug-resistant Bak-deficient cancer;

and wherein the multidrug-resistant apoptosis-deficient cancer is resistant against at least taxol and selected from a multidrug-resistant lung cancer, multidrug-resistant breast cancer, multidrug-resistant ovarian cancer or multidrug-resistant colon cancer.

2. The method of claim 1, wherein the quinonemethide triterpenoid has a structure of Formula (II):

Formula (II)

wherein
$R^1$ is selected from —CH$_3$ or —CH$_2$OH;
$R^2$ is —COOH; and
$R^3$ is selected from —OH, =O or —H.

3. The method of claim 1, wherein the quinonemethide triterpenoid has a structure of Formula (IIIa):

Formula (IIIa)

4. The method of claim 3, wherein the quinonemethide triterpenoid has a structure of Formula (IIIb):

Formula (IIIb)

5. The method of claim 1, wherein the quinonemethide triterpenoid is administered in combination with an effective amount of at least one chemotherapeutic compound, which chemotherapeutic compound is a compound selected from the group consisting of a topoisomerase-II inhibitor, an anthracycline, a coordination complex of platinum, a taxane, a protein kinase inhibitor, a vinca alkaloid, a topoisomerase-I inhibitor and a nucleotide or precursor.

6. The method of claim 5, wherein the chemotherapeutic compound is selected from the group consisting of taxol, doxorubicin, cisplatin, etoposide and staurosporine.

7. The method of claim 5, wherein the quinonemethide triterpenoid has a structure of Formula (IIIa) or (IIIb):

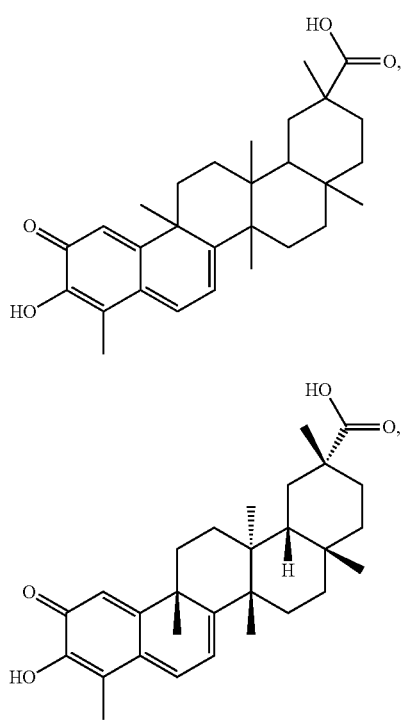

and wherein the chemotherapeutic compound is taxol.

8. The method of claim 5, wherein the chemotherapeutic compound is administered simultaneously with the quinonemethide triterpenoid.

9. A method for specifically targeting cancer cells with multidrug-resistance comprising the step of contacting a population of cancer cells which are multidrug-resistant apoptosis-deficient cancer cells with a decreased pro-apoptotic protein activity with a quinonemethide triterpenoid or a salt, solvate or anhydrate thereof, wherein the quinonemethide triterpenoid has a structure of Formula (I): Formula (I), wherein - - represents a single or double bond; —$R^1$ is selected from —$CH_3$, —$CH_2OH$, —OH or —H;
$R^2$ is selected from —$CH_3$, —$CH_2OH$, —OH—COOH, =$CH_2$ or H;
$R^3$ is selected from —OH, =O or —H; $R^4$ is selected from —OH or —H; —$R^5$ is selected from —OH or —H; and $R^6$ is selected from =O or —OH; wherein the multidrug-resistant apoptosis-deficient cancer cells are selected from at least one of multidrug-resistant p53-deficient cancer cells, multidrug-resistant Bax-deficient cancer cells or multidrug-resistant Bak-deficient cancer cells; and wherein the multidrug-resistant apoptosis-deficient cancer cells are resistant against at least taxol and selected from multidrug-resistant lung cancer cells, multidrug-resistant breast cancer cells, multidrug-resistant ovarian cancer cells or multidrug-resistant colon cancer cells.

10. The method of claim 9, wherein the quinonemethide triterpenoid has a structure of Formula (IIIa) or (IIIb):

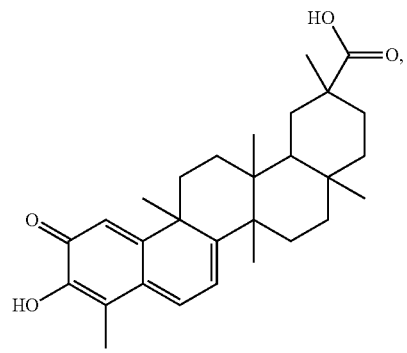

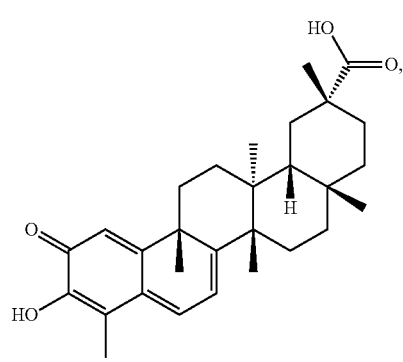

and wherein the cancer cells are contacted with between 0.1 µM and 8 µM of said quinonemethide triterpenoid.

11. A method of potentiating the activity of a chemotherapeutic compound in multidrug-resistant apoptosis-deficient cancer cells with a decreased pro-apoptotic protein activity comprising contacting the multidrug-resistant apoptosis-deficient cancer cells with (i) a quinonemethide triterpenoid; and (ii) a chemotherapeutic compound, which chemotherapeutic compound is selected from the group consisting of a topoisomerase-II inhibitor, an anthracycline, a coordination complex of platinum, a taxane, a protein kinase inhibitor, a vinca alkaloid, a topoisomerase-I inhibitor and a nucleotide or precursor, and wherein the multidrug-resistant apoptosis-deficient cancer cells are selected from at least one of multidrug-resistant p53-deficient cancer cells, multidrug-resistant Bax-deficient cancer cells or multidrug-resistant Bak-deficient cancer cells, wherein the multidrug-resistant apoptosis-deficient cancer cells are resistant against the chemotherapeutic compound at least taxol and selected from multidrug-resistant lung cancer cells, multidrug-resistant breast cancer cells, multidrug-resistant ovarian cancer cells or multidrug-resistant colon cancer cells, and wherein the quinonemethide triterpenoid has a structure of Formula (I): Formula (I), wherein - - represents a single or double bond; —$R^1$ is selected from —$CH_3$, —CH2OH, —OH or —H; $R^2$ is selected from —$CH_3$, —$CH_2OH$, —OH, —COOH, =$CH_2$ or —H; $R^3$ is selected from —OH, =O or —H; $R^4$ is selected from —OH or —H; $R^5$ is selected from —OH or —H; and $R^6$ is selected from =O or —OH.

12. The method of claim 11, wherein the multidrug-resistant apoptosis-deficient cancer cells are contacted with the chemotherapeutic compound simultaneously with the quinonemethide triterpenoid.

13. The method of claim 11, wherein the chemotherapeutic compound is taxol.

* * * * *